US006028052A

United States Patent [19]
Heyman et al.

[11] Patent Number: 6,028,052
[45] Date of Patent: *Feb. 22, 2000

[54] TREATING NIDDM WITH RXR AGONISTS

[75] Inventors: Richard A. Heyman, Encinitas; Rosemary Cesario; Ranjan Mukherjee, both of San Diego, all of Calif.

[73] Assignee: Ligand Pharmaceuticals Incorporated, San Diego, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/710,309

[22] Filed: Sep. 17, 1996

Related U.S. Application Data

[60] Provisional application No. 60/021,839, Jul. 10, 1996, provisional application No. 60/018,318, May 24, 1996, provisional application No. 60/009,884, Jan. 10, 1996, provisional application No. 60/004,897, Oct. 6, 1995, and provisional application No. 60/003,869, Sep. 18, 1995.

[51] Int. Cl.$^7$ .................. A61K 38/28; A61K 31/435; A61K 31/44; A61K 31/425; A61K 31/19

[52] U.S. Cl. .................. 514/3; 514/277; 514/299; 514/342; 514/367; 514/369; 514/370; 514/569; 514/725

[58] Field of Search .................. 514/725, 369, 514/299, 342, 367, 370, 3, 277, 569

[56] References Cited

U.S. PATENT DOCUMENTS

| | | |
|---|---|---|
| 4,981,784 | 1/1991 | Evans et al. . |
| 4,981,787 | 1/1991 | Baram . |
| 5,071,773 | 12/1991 | Evans et al. . |
| 5,219,888 | 6/1993 | Katocs et al. .................. 514/560 |
| 5,298,429 | 3/1994 | Evans et al. . |
| 5,399,586 | 3/1995 | Davies et al. . |
| 5,455,265 | 10/1995 | Chandraratna .................. 514/448 |
| 5,466,861 | 11/1995 | Dawson et al. . |
| 5,506,102 | 4/1996 | McDonnell . |
| 5,594,015 | 1/1997 | Kurtz et al. .................. 514/369 |
| 5,728,739 | 3/1998 | Aihaud et al. . |
| 5,827,897 | 10/1998 | Aihaud et al. . |

FOREIGN PATENT DOCUMENTS

| | | |
|---|---|---|
| 2034220 | 1/1991 | Canada . |
| A-552624 | 7/1993 | European Pat. Off. . |
| A-698392 | 2/1996 | European Pat. Off. . |
| 89/05355 | 6/1989 | WIPO . |
| 91/06677 | 5/1991 | WIPO . |
| 92/20642 | 11/1992 | WIPO . |
| 93/10094 | 5/1993 | WIPO . |
| 93/10166 | 5/1993 | WIPO . |
| 93/11235 | 6/1993 | WIPO . |
| 93/11755 | 6/1993 | WIPO . |
| 93/21146 | 10/1993 | WIPO . |
| A-93/21146 | 10/1993 | WIPO . |
| 93/23431 | 11/1993 | WIPO . |
| 94/15901 | 7/1994 | WIPO . |
| 94/15902 | 7/1994 | WIPO . |
| 94/23068 | 10/1994 | WIPO . |
| 95/18380 | 7/1995 | WIPO . |
| 96/05165 | 2/1996 | WIPO . |
| 96/20913 | 7/1996 | WIPO . |
| 96/20914 | 7/1996 | WIPO . |

OTHER PUBLICATIONS

Tontonoz, et al. "MPPARγ2: tissue–specific regulator of an adipocyte enhancer" *Genes & Development* 8: 1224–1234 (1994).

Boehm, et al. "Design and Synthesis of Potent X Receptor Selective Ligands that Induce Apoptosis in Leukemia Cells" *J. Med. Chem.* 38: 3146–3155 (1995).

Lehmann, et al. An Antidiabetic Thiazolidinedione Is a High Affinity Ligand for Peroxisome Proliferator–activated Receptor γ (PPARγ)*, *J. Biol. Chem.* 270(22): 12953–12956 (1995).

Safonova, et al. "Fatty Acids and Retinoids Act Synergistically on Adipose Cell Differentiation" *Biochem. and Biophysical Research Communications* 204(2): 498–504 (1994).

Amri, et al. "Regulation of adipose cell differentiation. I. Fatty acids are inducers of the aP2 gene expression" *J. Lipid Research* 32: 1449–1456 (1991).

Amri, et al. "Regulation of adipose cell differentiation. II. Kinetics of induction of the aP2 gene by fatty acids and modulation of dexamethasone" *J. Lipid Research* 32: 1457–1463 (1991).

Antrast, et al. "Adipsin Gene Expression in 3T3–F442A Adipocytes Is Postranscriptionally Down–regulated by Retinoic Acid" *J. Biol. Chem.* 266(2): 1157–1161 (1991).

Boehm, et al. "Synthesis and Structure–Activity Relationships of Novel Retinoid X Receptor–Selective Retinoids" *J. Med. Chem.* 37: 2930–2941 (1994).

Boehm, et al. "Design and Synthesis of Potent Retinoid X Receptor Selective Ligands That Induce Apoptosis in Leukemia Cells" *J. Med. Chem.* 38: 3146–3155 (1995).

Grimaldi, et al. "Induction of aP2 gene expression by nonmetabolized long–chain fatty acids" *Proc. Natl. Acad. Sci. USA* 89: 10930–10934 (1992).

Kees, et al. "Studies on New Acidic Azoles as Glucose–Lowering Agents in Obese, Diabetic db/db Mice" *J. Med. Chem.* 38: 617–628 (1995).

Kliewer, et al. "Convergence of 9–cis retinoic acid and peroxisome proliferator signalling pathways through heterodimer formation of their receptors" *Nature* 358: 771–774 (1992).

Lehmann, et al. An Antidiabetic Thiazolidinedione Is a High Affinity Ligand for Peroxisome Proliferator–activated Receptor γ (PPARγ)* *J. Biol. Chem.* 270(22): 12953–12956 (1995).

(List continued on next page.)

*Primary Examiner*—Raymond Henley, III
*Attorney, Agent, or Firm*—Lyon & Lyon LLP

[57] ABSTRACT

This invention relates to methods and compositions for the treatment of non-insulin-dependent diabetes mellitus using an RXR agonist alone or in combination with a PPARγ agonist such as a thiazolidinedione compound.

162 Claims, 10 Drawing Sheets

OTHER PUBLICATIONS

Mukherjee, et al. "Human and Rat Peroxisome Proliferator Activated Receptors (PPARs) Demonstrate Similar Tissue Distribution but Different Responsiveness to PPAR Activators" *J. Steroid Biochem. Molec. Biol.* 51(3/4): 157–166 (1994).

Safonova, et al. "Retinoids are positive effectors of adipose cell differentiation" *Molecular and Cellular Endocrinology* 104: 201–211 (1994).

Salazar–Olivo, et al. "Inhibition of 3T3 Adipogenesis by Retinoic Acid is Not Mediated by Cytoplasmic Retinoic Acid–Binding Protein" *Biochemical and Biophysical Research Communications* 204(1): 257–263 (1994).

Tontonoz, et al. "Stimulation of Adipogenesis in Fibroblasts by PPARγ2, a Lipid–Activated Transcription Factor" *Cell* 79: 1147–1156 (1994).

Willson, et al. "The Structure–Activity Relationship between Peroxisome Proliferator–Activated Receptor γ Agonism and the Antihyperglycemic Activity of Thiazolidinediones" *J. Med. Chem.* 39: 665–668 (1996).

Young, et al. "Repeat Treatment of Obese Mice With BRL 49653, a New and Potent Insulin Sensitizer, Enhances Insulin Action in White Adipocytes" *Diabetes* 44: 1087–1092 (1995).

Fingl et al., in *The Pharmacological Basis of Therapeutics*, 1975, Ch. 1, p. 1.

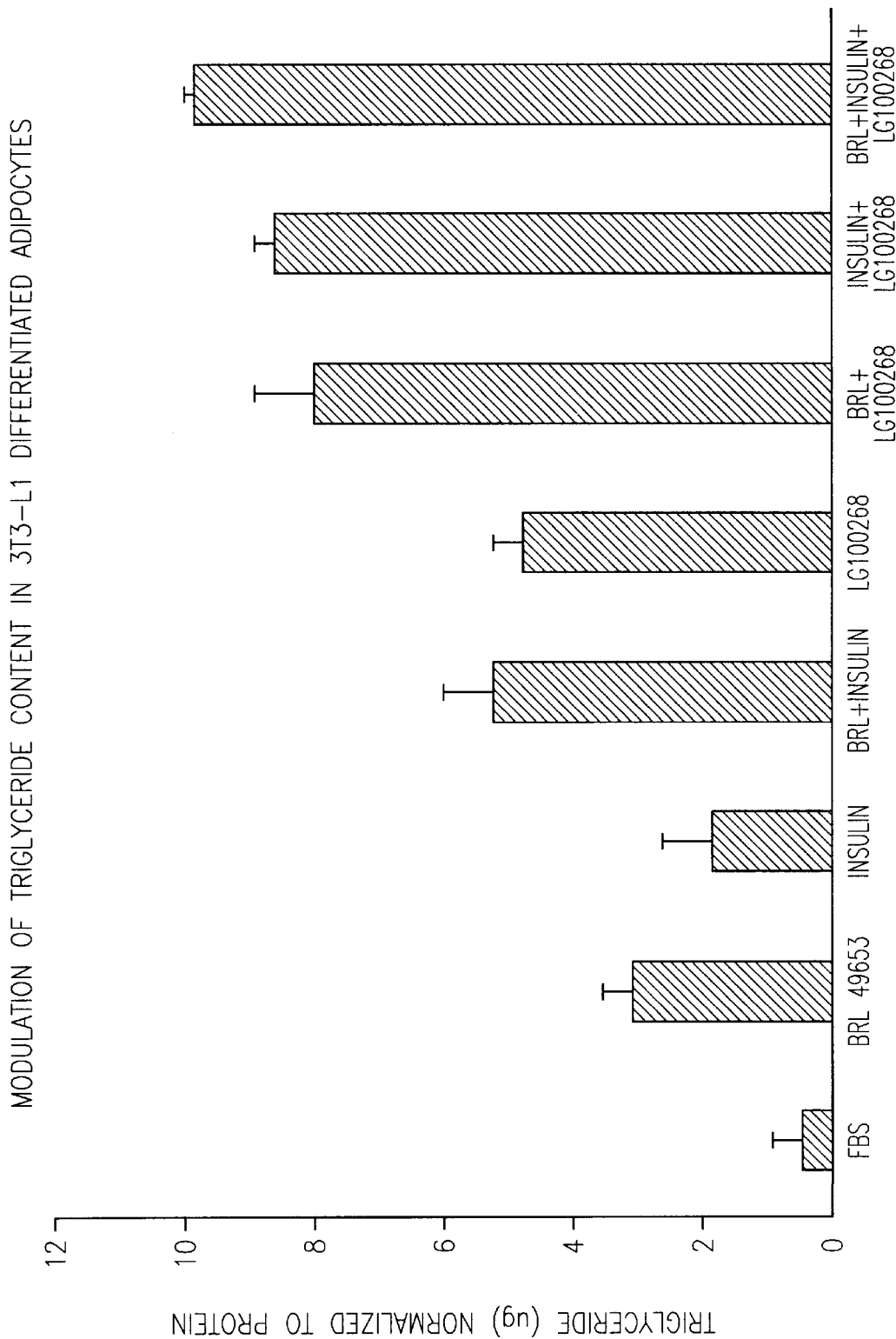

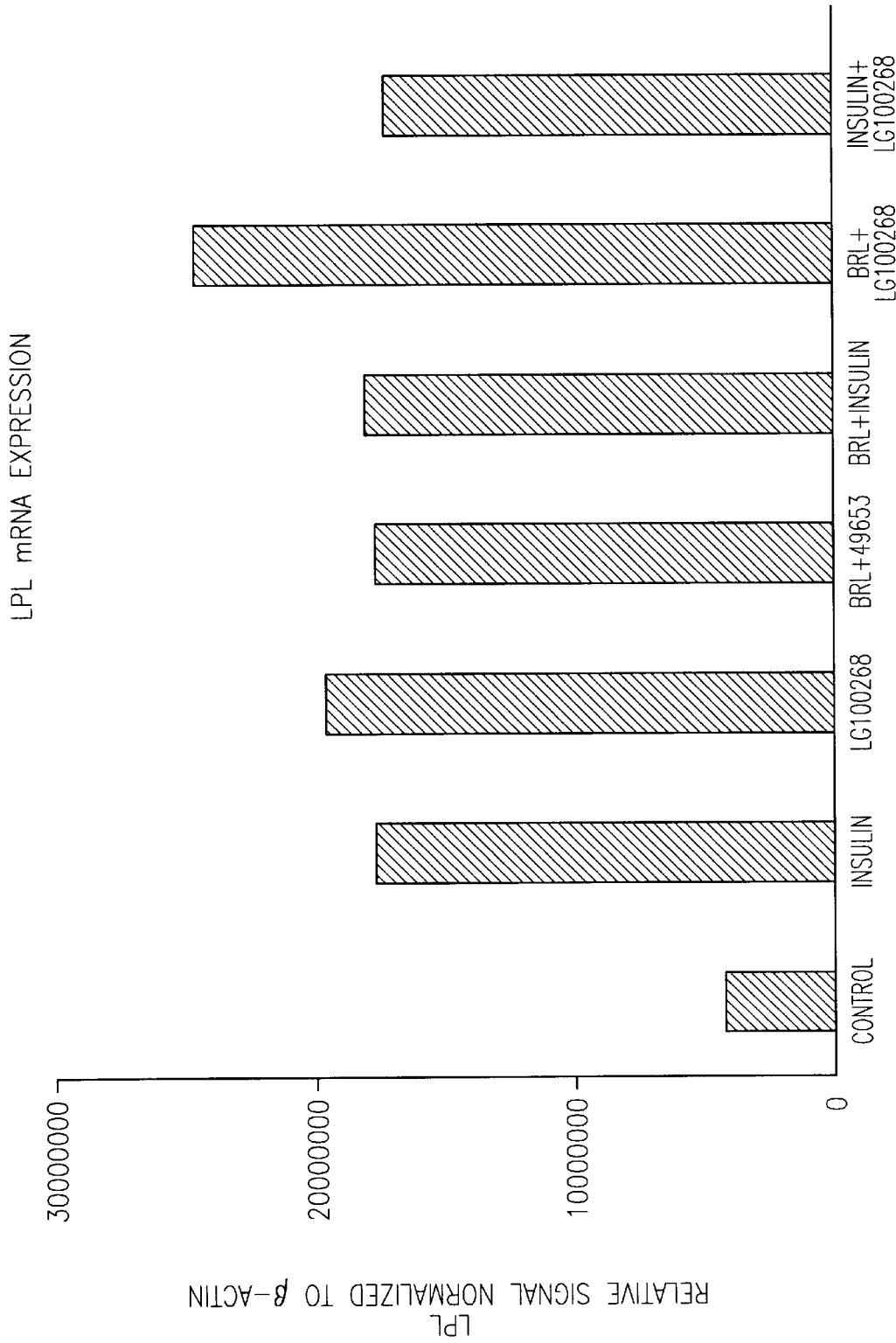

TREATING NIDDM WITH RXR AGONISTS

RELATED APPLICATIONS

This application is related to provisional application Ser. Nos. 60/021,839, filed Jul. 10, 1996; 60/003,869—filed Sep. 18, 1995; 60/004,897—filed Oct. 6, 1995; 60/009,884—filed Jan. 10, 1996; 60/018,318—filed May 24, 1996; and 60/021,839—filed Jul. 10, 1996 which are incorporated herein by reference in their entirety, including any drawings and figures.

FIELD OF THE INVENTION

This invention relates to methods and pharmaceutical compounds for treating diabetes and related symptoms.

BACKGROUND OF THE INVENTION

Non-insulin-dependent diabetes mellitus (NIDDM, type II diabetes) is characterized by abnormalities in insulin secretion and insulin action. NIDDM constitutes 90–95% of the approximately 6 million diagnosed diabetics in the United States. NIDDM is characterized by hyperglycemia, the result of insulin resistance in peripheral tissues (skeletal muscle and adipose tissue), where insulin-stimulated uptake/utilization of glucose is blunted, and in liver, where insulin suppression of glucose output is insufficient. These impairments in insulin action play an important role in the development of elevated fasting blood glucose and glucose intolerance.

Diet and exercise are first-line therapy for NIDDM patients. NIDDM patients also take oral hypoglycemic drugs to control blood glucose levels. The most widely used hypoglycemic agents are various formulations of insulin and sulfonylureas. A major drawback with these therapies is the occurrence of potentially life-threatening hypoglycemia due to hyperinsulinemia.

The hyperinsulinemia that can occur with these therapies is also associated with an elevated risk of cardiovascular disease, a major killer of diabetics. Therefore, a need exists for antidiabetic drugs which do not increase circulating insulin concentrations.

A new class of compounds, thiazolidinediones, have been documented to effect antihyperglycemic activity by increasing insulin action rather than by promoting insulin secretion. Thiazolidinediones ameliorate insulin resistance and normalize plasma glucose and insulin (where elevated) without causing a hypoglycemic state, even at very high doses. The thiazolidinedione insulin sensitizers, e.g., ciglitazone, englitazone, pioglitazone, BRL 49653 (5-[[4-[2-(methyl-2-pyridinylamino)ethoxy]phenyl]methyl]-2,4-thiazolidinedione), and troglitazone, enhance insulin-mediated suppression of hepatic glucose output and insulin-stimulated glucose uptake and utilization by adipose tissue. Thiazolidinediones also change glucose transporter (e.g. Glut 4) expression to contribute to increased insulin responsiveness.

SUMMARY OF THE INVENTION

Applicant has found that RXR agonists mimic or enhance the antidiabetic effects of thiazolidinedione compounds. RXR agonists activate the transcriptional activity of RXR/PPARγ heterodimers, increase insulin stimulated glucose uptake, lower the level of triglyceride, suppress the level of insulin, and increase the level of HDL cholesterol. Two RXR agonists have been shown to lower glucose, triglycerides and insulin levels in two established animal models of NIDDM, i.e. the ob/ob and db/db mice. Therefore, RXR agonists may be used as insulin sensitizers or insulin mimetics in the treatment of NIDDM and related symptoms.

In addition, the combination of an RXR agonist and a PPARγ agonist, such as a thiazolidinedione, achieves synergistic activation of the RXR/PPARγ heterodimers so as to enhance adipogenic and antidiabetic effects of PPARγ. In db/db mice, the combination of an RXR agonist and a PPARγ agonist was shown to lower the level of glucose more than individual compounds did.

Therefore, the present invention relates to methods and compositions for treating a host having NIDDM or insulin resistant diabetes by administering to the host a composition containing a pharmaceutically effective amount of an activator of the RXR/PPARγ heterodimer, including, but not limited to, an RXR agonist. The host may be a human patient or an animal model of human NIDDM. The compositions of this invention are adapted to cure, improve or prevent one or more symptoms of NIDDM in the host. A preferred drug is highly potent and selective with low toxicity. In this regard, those skilled in the art will recognize NIDDM as an example of a metabolic disease that can be treated with the RXR agonist-containing compounds and compositions of the present invention. Other examples of metabolic diseases treatable with the compounds and compositions of the present invention include, but are not limited to, obesity and thyroid hormone abnormalties.

By "pharmaceutically effective amount" is meant an amount of a pharmaceutical compound or composition having a therapeutically relevant effect on NIDDM. A therapeutically relevant effect relieves to some extent one or more symptoms of NIDDM in a patient or returns to normal either partially or completely one or more physiological or biochemical parameters associated with or causative of NIDDM, e.g. increasing the sensitivity of cellular response to circulating insulin, curing, reducing, or preventing one or more clinical symptoms of NIDDM, including, but not limited to, hyperglycemia, hyperinsulinemia and hypertriglyceridemia. In a preferred embodiment, a pharmaceutically effective amount of a compound or composition means an amount that increases the uptake of glucose by adipose tissue or muscle tissue. In another preferred embodiment, a pharmaceutically effective amount of a compound or composition means an amount that increases the uptake of triglyceride by adipose tissue.

By "activator of the RXR/PPARγ heterodimer" is meant a compound or composition which when combined with the RXR/PPARγ heterodimer increases the transcriptional regulation activity of the heterodimer, as measured by an assay known to one skilled in the art, including, but not limited to, the "co-transfection" or "cis-trans" assays described or disclosed in U.S. Pat. Nos. 4,981,784, 5,071,773, 5,298,429, 5,506,102, WO89/05355, WO91/06677, WO92/05447, WO93/11235, WO95/18380, PCT/US93/04399, PCT/US94/03795 and CA 2,034,220, which are incorporated by reference herein. It includes, but is not limited to, compounds that bind RXR, PPARγ, or both.

By "RXR agonist" is meant a compound or composition which when combined with RXR homodimers or heterodimers increases the transcriptional regulation activity of RXR, as measured by an assay known to one skilled in the art, including, but not limited to, the "co-transfection" or "cis-trans" assays described or disclosed in U.S. Pat. Nos. 4,981,784, 5,071,773, 5,298,429, 5,506,102, WO89/05355, WO91/06677, WO92/05447, WO93/11235, WO95/18380, PCT/US93/04399, PCT/US94/03795 and CA 2,034,220, which are incorporated by reference herein. It includes, but is not limited to, compounds that preferentially activate RXR over RAR (i.e. RXR specific agonists), and compounds that activate both RXR and RAR (i.e. pan agonists). It also includes compounds that activate RXR in a certain cellular context but not others (i.e. partial agonists). Compounds disclosed or described in the following articles, patents and patent applications which have RXR agonist activity are incorporated by reference herein: U.S. Pat. Nos. 5,399,586 and 5,466,861, WO96/05165, PCT/US95/16842, PCT/US95/16695, PCT/US93/10094, WO94/15901, PCT/US92/11214, WO93/11755, PCT/US93/10166, PCT/US93/10204, WO94/15902, PCT/US93/03944, WO93/21146, provisional applications 60,004,897 and 60,009,884, Boehm, et al. *J. Med. Chem.* 38(16):3146–3155, 1994, Boehm, et al. *J. Med. Chem.* 37(18):2930–2941, 1994, Antras et al., *J. Biol. Chem.* 266:1157–1161 (1991), Salazar-Olivo et al., *Biochem. Biophys. Res. Commun.* 204:157–263 (1994) and Safanova, *Mol. Cell. Endocrin.* 104:201–211 (1994). RXR specific agonists include, but are not limited to, LG 100268 (i.e. 2-[1-(3,5,5,8,8-pentamethyl-5,6,7,8-tetrahydro-2-naphthyl)-cyclopropyl]-pyridine-5-carboxylic acid) and LGD 1069 (i.e. 4-[(3,5,5,8,8-pentamethyl-5,6,7,8-tetrahydro-2-naphthyl)-2-carbonyl]-benzoic acid), and analogs, derivatives and pharmaceutically acceptable salts thereof. The structures and syntheses of LG 100268 and LGD 1069 are disclosed in Boehm, et al. *J. Med. Chem.* 38(16):3146–3155, 1994, incorporated by reference herein. Pan agonists include, but are not limited to, ALRT 1057 (i.e. 9-cis retinoic acid), and analogs, derivatives and pharmaceutically acceptable salts thereof.

In a preferred embodiment, the pharmaceutical composition also contains a pharmaceutically effective amount of a PPARγ agonist. Alternatively, a second composition containing a pharmaceutically effective amount of a PPARγ agonist is administered to the host separately. In a further preferred embodiment, a compound having agonist activity for both RXR and PPARγ is used.

By "PPARγ agonist" is meant a compound or composition which when combined with PPARγ increases a reaction typical for the receptor, e.g., transcriptional regulation activity, as measured by an assay known to one skilled in the art, including, but not limited to, the "co-transfection" or "cis-trans" assays described or disclosed in U.S. Pat. Nos. 4,981,784 and 5,071,773 and Lehmann, et al., *J. Biol. Chem.* 270:12953–12956 (1995), which are incorporated by reference herein. A preferred PPARγ agonist is a thiazolidinedione compound, including, but not limited to, BRL 49653, troglitazone, pioglitazone, ciglitazone, WAY-120,744, englitazone, AD 5075, darglitazone, and analogs, derivatives and pharmaceutically acceptable salts thereof. Compounds disclosed in Tontonez et al., *Genes & Develop.* 8:1224–1234 (1994), Tontonez et al., *Cell* 79:1147–1156 (1994), Lehmann et al., *J. Biol. Chem.* 270(22):1–4, 1995, Amri et al., *J. Lipid Res.* 32:1449–1456 (1991), Amri et al., *J. Lipid Res.* 32:1457–1463, (1991) and Grimaldi et al., *Proc. Natl. Acad. Sci. USA* 89:10930–10934 (1992) are incorporated by reference herein.

In a further preferred embodiment, the pharmaceutical composition also contains a pharmaceutically effective amount of insulin, insulin derivative, insulin secretagogue, insulin sensitizer, or insulin mimetic. Alternatively, a composition containing a pharmaceutically effective amount of insulin, insulin derivative, insulin secretagogue, insulin sensitizer, or insulin mimetic is administered to the host separately.

A composition containing a pharmaceutically effective amount of an active ingredient may be administered orally or systemically to a host. In a preferred embodiment, it is administered orally.

In another aspect, this invention features a pharmaceutical composition for treating NIDDM containing a pharmaceutically effective amount of an RXR agonist; and a pharmaceutically acceptable carrier adapted for a host having NIDDM. In a preferred embodiment, the pharmaceutical composition also includes a pharmaceutically effective amount of insulin, insulin derivative, insulin secretagogue, insulin sensitizer, insulin mimetic or PPARγ agonist.

In a preferred embodiment, the composition is held within a container which includes a label stating to the effect that the composition is approved by the FDA in the United States (or an equivalent regulatory agency in a foreign country) for treating NIDDM or for treating hyperglycemia, hyperinsulinemia or hypertriglyceridemia. Such a container provides a therapeutically effective amount of the active ingredient to be administered to a host.

In another aspect, this invention features methods for screening for candidate compounds useful for treating NIDDM. These methods select compounds or compositions which when combined with the RXR/PPARγ heterodimer increase the transcriptional regulation activity of the heterodimer, as measured by an assay known to one skilled in the art, including, but not limited to, the "co-transfection" or "cis-trans" assays described or disclosed in U.S. Pat. Nos. 4,981,784, 5,071,773, 5,298,429, 5,506,102, WO89/05355, WO91/06677, WO92/05447, WO93/11235, WO95/18380, PCT/US93/04399, PCT/US94/03795 and CA 2,034,220, which are incorporated by reference herein. In one example, a candidate compound such as a potential RXR agonist is administered to an adipocyte or a preadipocyte. The level of lipid in the cell is measured, and an increased accumulation of lipid after the treatment with the candidate compound indicates that the candidate compound is useful for treating NIDDM. In preferred embodiments, the level of lipid is measured by oil red O staining or detecting the level of triglyceride in the cell.

In another example, a candidate compound such as a potential RXR agonist is administered to an adipocyte or a preadipocyte and the transcription level of a adipocyte specific gene (e.g. lipoprotein lipase gene or PPARγ gene) is measured. An increased transcription of the adipocyte specific gene after the treatment with the candidate compound indicates that the candidate compound is useful for treating NIDDM.

In yet another example, a candidate compound such as a potential RXR agonist is administered to an adipocyte or a preadipocyte and the level of glucose uptake is measured. An increased glucose uptake after the treatment with the candidate compound indicates that the candidate compound is useful for treating NIDDM. Alternatively, both the candidate compound and insulin are administered to the cell and the level of glucose uptake is compared to that in the same cell treated with insulin alone. A higher level of glucose uptake in the cell treated by the candidate compound and insulin indicates that the candidate compound is an insulin sensitizer and useful for treating NIDDM.

Other features and advantages of the invention will be apparent from the following detailed description of the invention, and from the claims.

BRIEF DESCRIPTION OF THE DRAWINGS

FIG. 1a is a graph showing the extent of adipocyte differentiation in 3T3-LI cells as measured by the levels of triglyceride in 3T3-LI preadipocytes treated with various combinations of an RXR agonist (LG 100268), a PPARγ agonist (thiazolidinedione compound BRL 49653), and insulin. The retinoid and BRL 49653 were used at 1 μM.

FIG. 2a is a graph showing the level of LPL mRNA in 3T3-LI cells treated with various combinations of an RXR agonist (LG 100268), a PPARγ agonist (thiazolidinedione compound BRL 49653), and insulin. The retinoid and BRL 49653 were used at 1 μM.

DETAILED DESCRIPTION OF THE INVENTION

Figure 1B:
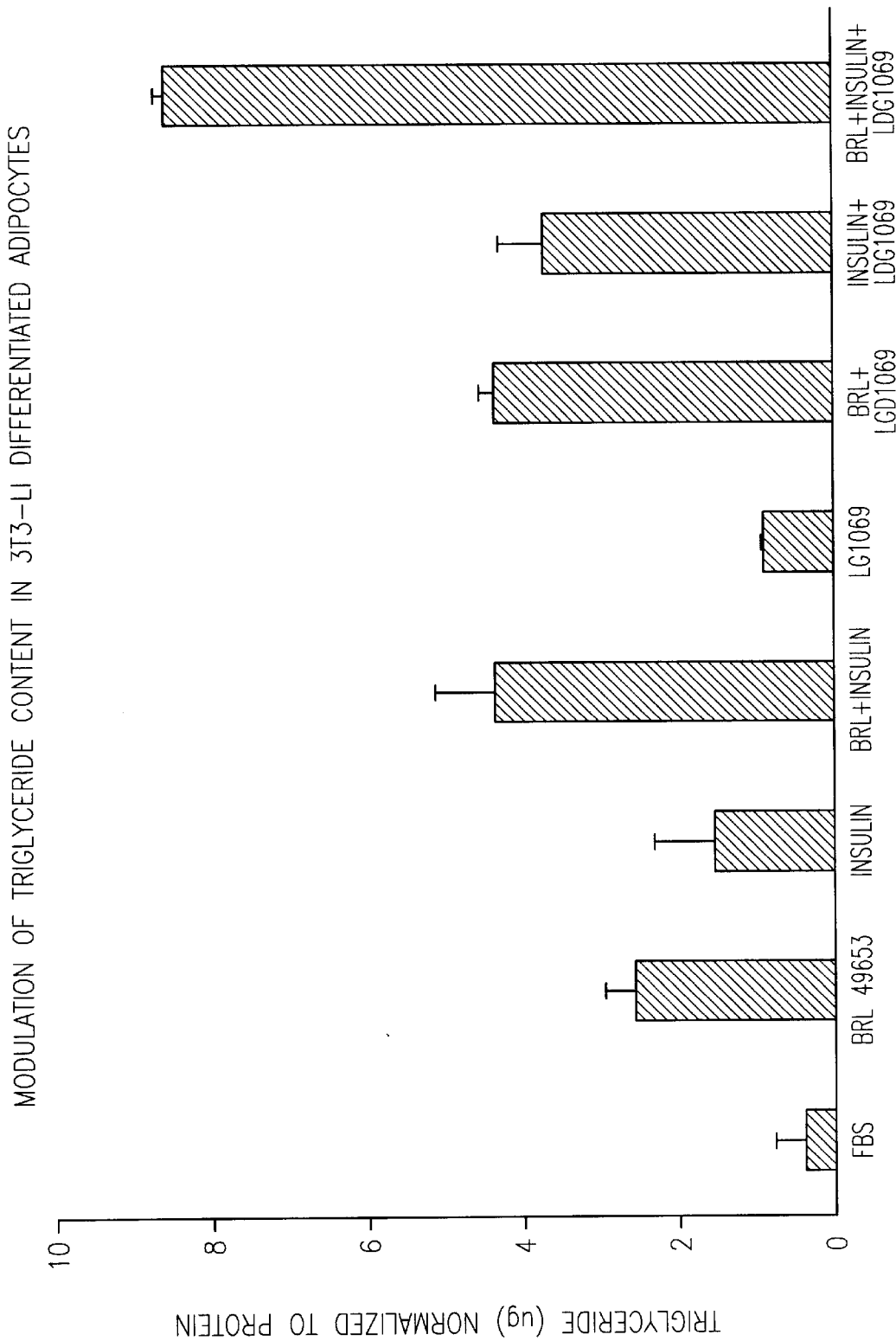
FIG. 1b is a graph showing the extent of adipocyte differentiation in 3T3-LI cells as measured by the level of triglyceride in 3T3-LI preadipocytes treated with various combinations of an RXR agonist (LGD 1069), a PPARγ agonist (thiazolidinedione compound BRL 49653), and insulin. The retinoid and BRL 49653 were used at 1 μM.

TZD achieves antidiabetic and adipogenic effects through PPARγ

Thiazolidinediones are insulin sensitizers that significantly reduce glucose and lipid levels in animal models of NIDDM and obesity (Kees, et al., *J. Medicinal Chem.* 38(4):617–628, 1995; Willson, et al., *J. Medicinal Chem.* 39(3):665–668, 1996; Young, et al. *Diabetes* 44:1087–1092, 1995). Thiazolidinediones improve glucose utilization without stimulating insulin release.

For example, repeated administration of BRL 49653 to obese mice improves glycemic control by increasing insulin responsiveness of target tissues. BRL 49653 potentiates insulin-stimulated glucose transport in adipocytes from insulin-resistant obese mice, both by increasing insulin receptor number and by facilitating translocation of GLUT4, from an expanded intracellular pool, to the cell surface.

Thiazolidinediones are also selective PPARγ agonists (Lehmann, et al. *J. Biol. Chem.* 270(22):1–4, 1995). Comparison of the $EC_{50}$ for activation of PPARγ with the minimum effective dose (MED) for anti-hyperglycemic activity revealed a significant correlation. The correlation between in vitro PPARγ activity and in vivo antihyperglycemic activity of thiazolidinediones implicates PPARγ as the molecular target for the antidiabetic effects of thiazolidinediones.

PPARγ is a member of the nuclear receptor superfamily of ligand-activated transcription factors. It is expressed in an adipose-specific manner and its expression is induced early during the differentiation of several preadipocyte cell lines. Forced expression of PPARγ in fibroblasts resulted in adipocyte differentiation.

In addition to insulin sensitizing activity, thiazolidinediones have marked adipogenic effects on preadipocyte and mesenchymal stem cells (Tontonoz, et al., *Cell* 79:1147–1156, 1994). Treatment of C3H/10T1/2 cells with BRL 49653 resulted in efficient adipocyte differentiation, showing that ligand-mediated activation of PPARγ is sufficient to initiate the adipogenic signaling cascade in a mesenchymal stem cell line. PPARγ is the molecular target for the adipogenic effects of thiazolidinediones.

Adipogenesis plays a role in the development of NIDDM, which is characterized by not only unbalanced glucose homeostasis, but also elevated levels of circulating lipids. Increases in lipid levels have been shown to interfere with glucose disposal.

Adipocytes are highly specialized cells that play a critical role in lipid metabolism and energy homeostasis. Their primary role is to store triglycerides in times of caloric excess and to mobilize this reserve during periods of nutritional deprivation.

Adipocyte differentiation is characterized by a coordinate increase in adipocyte-specific gene expression. PPARγ is specifically expressed in adipocytes. Its expression is induced early during the course of differentiation of several preadipocyte cell lines. Forced expression of PPARγ in fibroblasts resulted in adipocyte differentiation.

Synergistic effects of RXR and PPARγ on adipogenesis

Expression of PPARγ is induced early during the differentiation of cultured adipocyte cell lines and is expressed at very high levels specifically in adipose tissue. PPARγ regulates adipogenesis by modulating the transcription of other adipocyte-specific genes, e.g. adipocyte P2 gene (aP2 gene). aP2 gene encodes an intracellular lipid-binding protein and is expressed exclusively in adipose cells.

A 518-bp DNA fragment from the 5'-flanking region of the aP2 gene has been identified as an enhancer that directs high-level adipocyte-specific gene expression in both cultured cells and transgenic mice. A pair of elements in the aP2 enhancer, ARE6 and ARE7, bind a nuclear factor termed ARF6 that is detected only in nuclear extracts derived from adipocytes. The ARF6-binding sites are both necessary and sufficient for adipocyte-specific expression, suggesting that the trans-acting factor ARF6 functions as a differentiation-dependent and tissue-specific switch for the aP2 enhancer (Tontonoz, et al. *Genes & Development,* 8:1224–1234, 1994).

The ARF6 recognition sequence resembles a type of nuclear hormone receptor-binding site known as DR-1 (direct repeat with 1-nucleotide spacer). This motif has been shown to preferentially bind heterodimers of RXR and COUP-TF and heterodimers of RXR and the PPARs. DNA mobility retardation experiments using various HRE sequences as competitor demonstrated that ARF6 preferentially recognizes DR-1 sites.

ARF6 has been identified as a heterodimeric complex of RXRα and PPARγ. It has been shown that PPARγ and RXRα form heterodimers on ARF6-binding sites in vitro. Forced expression of these factors in transient transfections is sufficient to activate the adipocyte-specific aP2 enhancer in nonadipose cells such as fibroblasts. This activation is potentiated by peroxisome proliferators, fatty acids, and 9-cis retinoic acid. Antiserum to RXRα specifically inhibits ARF6 activity in adipocyte nuclear extracts.

Cotransfection of the RXRα expression vector and the PPARγ expression vector has a synergistic effect to activate the aP2 enhancer in nonadipose cells. Maximal activation of the aP2 enhancer is observed when both PPARγ, RXRα and their agonists are present.

Without being bound by any theory, applicant proposes that an RXR agonist affects glucose usage in tissues through the synergistic effects of RXR and PPARγ heterodimers. The RXR/PPARγ heterodimers, when activated by an RXR agonist or a combination of an RXR agonist and a PPARγ agonist, induce adipogenesis and modulates the levels of glucose and triglyceride uptake. Alternatively or in addition, the RXR/PPARγ heterodimers, when activated by an RXR agonist or a combination of an RXR agonist and a PPARγ agonist, regulate signaling molecules secreted by adipose tissue such as tumor necrosis factor-α or leptin, which in turn modulates glucose metabolism in other tissues.

Using RXR agonists to mimic or enhance the antidiabetic effects of thiazolidinediones PPARα, β and γ all form heterodimers with RXRs. These RXR/PPAR heterodimers bind to DNA and regulate transcription activity. RXR activators cooperate with PPARα activators to activate the activity of PPARα protein (Kliewer, et al. *Nature* 358:771–774 (1992) and Mukherjee, et al. *Steroid Biochem. Molec. Biol.* 51:157–166 (1994)).

In this invention, a similar synergistic activation was observed with a PPARγ activator and several RXR activators.

According to this invention, RXR agonists, e.g. LGD 1069, ALRT 1057 and LG 100268, may be utilized in the treatment of diabetes. We examined four independent parameters for the effects of RXR agonists, i.e. morphological changes, lipid accumulation, regulation of gene expression and increased glucose uptake.

Two pre-adipocyte cell lines were used to test the theory of RXR activation in the PPARγ/RXR heterodimer. 3T3-LI and C3H/10T1/2 cells were obtained from ATCC and are derived from mouse embryo. They are contact inhibited and can be induced to differentiate into adipocyte cells containing large lipid droplets within the cytoplasm. Adipocyte differentiation can be observed by oil red O staining which stains the lipid droplets within the cytoplasm red. The extent of adipocyte differentiation can then be monitored by microscope observation.

For a more quantitative assay and rapid screening of compounds, a 96-well plate assay was developed to quantitate the amount of triglyceride produced by the differentiating adipocytes. In this assay, cells are grown as a monolayer to confluence on a 96-well plate and treated with BRL 49653, insulin, and retinoids alone or in various combinations. These treatments induce differentiation to different extent in both 3T3-LI and C3H/10T1/2 cells. The level of triglyceride accumulation can then be measured via an enzymatic color reaction which can be read in a plate reader.

A third measure of adipocyte differentiation is to examine regulation of gene expression. The mRNA expression levels of both PPARγ and lipoprotein lipase (LPL) have been shown to be modulated during adipocyte differentiation. Northern blot analysis was used to dissect the molecular aspects of how retinoids effect target genes of differentiating adipocytes. PPARγ, lipoprotein lipase (LPL), and β-actin (loading control) MRNA levels were monitored after cells were treated with thiazolidinediones and retinoids.

A fourth indicator for the utility of a compound in treating NIDDM or insulin-resistant diabetes is the compound's ability to enhance insulin-stimulated glucose uptake. Labeled 2-deoxyglucose (2-DOG, a glucose analog) assay was performed with a preadipocyte cell line in the presence of insulin and a candidate compound to measure the level of 2-DOG incorporation.

A) Retinoid Modulation of Lipid Accumulation in 3T3-LI Cells Stained with Oil Red O Table 1 shows the percent of 3T3-LI cells that had differentiated into adipocytes as observed by oil red O staining assay. BRL 49653 and LG 100268 were used at 1 μM, insulin was used at 0.01 mg/ml. Wells treated with LG 100268 had bigger redder lipid droplets within the cytoplasm.

BRL 49653 and LG 100268 treatment alone induced 50% of the cells to differentiate into adipocytes. This was increased dramatically with the addition of insulin. Insulin in combination with BRL induced 80% of the 3T3-LI cells into adipocytes while the combination of insulin and LG 100268 induced 90% of the cells to differentiate. When BRL 49653 was used in combination with LG 100268, an RXR agonist, the amount of adipocytes differentiation was also increased dramatically. Other RXR agonists mimic the activity of LG 100268. For example, the addition of ALRT 1057 (pan agonist) or LGD 1069 (RXR specific agonist) in combination with BRL 49653 increased the amount of differentiation, albeit to a lesser extent than the strong RXR agonist LG 100268. The combination of insulin with BRL 49653 and LGD 1069 had a strong differentiating effect (95%) on the 3T3-LI cells.

B) Retinoid Modulation of Triglyceride Content in Differentiated Adipocytes

The retinoid modulation of lipid formation was quantitated by monitoring triglyceride formation. FIGS. 1a and 1b show triglyceride accumulation in 3T3-LI cells treated with a retinoid (LG 100268 or LGD 1069) alone or in combination with a thiazolidinedione and insulin. Retinoids and BRL 49653 were used at 1 μM, insulin was used at 0.01 mg/ml for all experimental combinations.

Insulin, BRL 49653 and retinoids all induced some triglyceride accumulation when used alone, with LG 100268 giving the largest response. The addition of retinoids (LGD 1069, LG 100268) with the thiazolidinedione (BRL 49653) to the assay increased the amount of triglyceride accumulation in 3T3-LI differentiating adipocytes. This was also observed when BRL 49653 or LG 100268 was used in combination with insulin. The largest accumulation of triglyceride was seen in the cells treated with LG 100268, BRL 49653 and insulin together. Similar results were observed when LGD 1069 replaced LG 100268 in the study. These results concur with those obtained in the oil red O staining assays.

C) PPARγ and LPL mRNA modulation in differentiating 3T3-LI cells

Figure 2B:
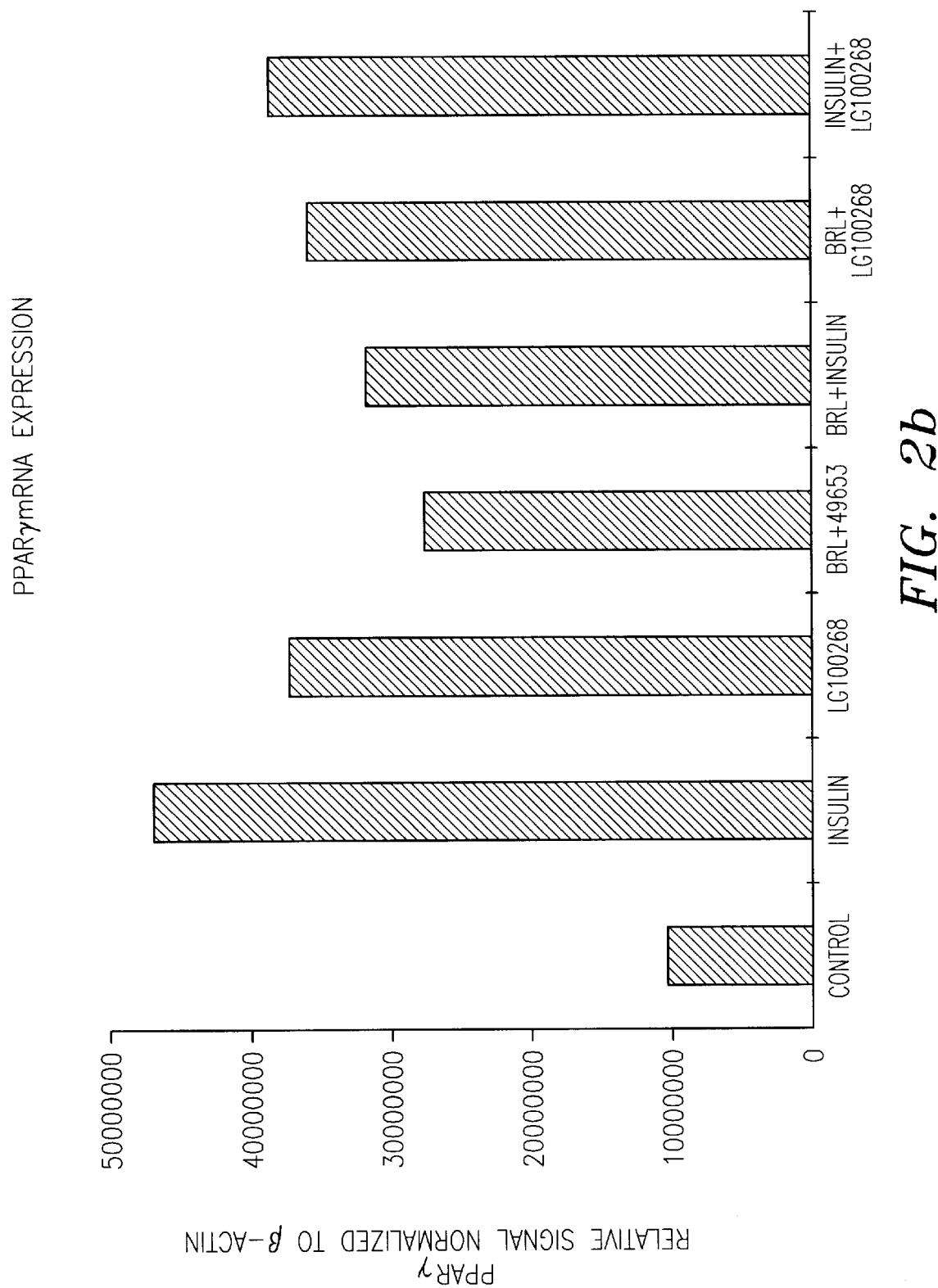
FIG. 2b is a graph showing the level of PPARγ mRNA in 3T3-LI cells treated with various combinations of an RXR agonist (LG 100268), a PPARγ agonist (thiazolidinedione compound BRL 49653), and insulin. The retinoid and BRL 49653 were used at 1 μM.

Adipocyte specific genes were monitored via northern blot analysis. FIGS. 2a and 2b show the expression pattern of LPL (lipoprotein lipase) mRNA and PPARγ mRNA in cells that were treated for 7 days with BRL 49653 (1 μM), LG 100268 (1 μM) and insulin (0.01 mg/ml), alone or in combination.

Northern blot analysis shows an increase in the relative signal normalized to β-actin of both LPL and PPARγ mRNA expression in cells treated with either compound alone. There was a three to five fold increase in mRNA levels for these adipocyte target genes demonstrating that transcriptional regulation occurs with treatment by insulin, BRL 49653 and LG 100268. Combination of insulin, BRL 49653 and LG 100268 did not further enhance the mRNA level.

These data demonstrate that, in 3T3-LI cells, RXR agonists induce adipocyte differentiation by themselves or in combination with thiazolidinediones or insulin. RXR agonists enhance the activity of thiazolidinediones and insulin. Three independent measurements support that RXR agonists contribute to the modulation of the RXR/PPARγ heterodimer in regulating adipocyte differentiation and useful in treating NIDDM.

D) LG 100268 enhances insulin stimulated glucose uptake in 3T3-LI cells

A murine preadipocyte cell line, 3T3-L1, is widely used to study glucose uptake, adipogenesis, and has been used in the characterization of thiazolidinediones and other PPARγ activators. Insulin stimulated uptake of labeled 2-deoxyglucose (2-DOG, a glucose analog) was observed in 3T3-L1 cells treated with BRL 49653 or LG 100268.

3T3-L1 cells were treated with BRL 49653 (10 μM) or LG 100268 (1 μM) for 10 days. Insulin was added to the cells at a concentration of 0.01 mg/ml for 5 days, thereafter no insulin was added. Labeled 2-deoxyglucose uptake assay was performed (Szalkowski, et al., *J. Endocrin.* 136:1474–1481, 1995). The level of incorporated labeled 2-DOG was normalized to the amount of total cellular protein. About 5-fold increase in 2-DOG uptake was observed in 3T3-L1 cells treated with BRL 49653 alone. About 2-fold increase in 2-DOG uptake was observed in 3T3-L1 cells treated with LG 100268 alone.

This experiment shows that an RXR agonist increases insulin mediated glucose uptake in 3T3-L1 cells like a known insulin sensitizer, a thiazolidinedione. It demonstrates directly that RXR agonists can be used to treat a major symptom of NIDDM, i.e. insulin resistance. Other RXR agonists useful for the treatment of NIDDM can be confirmed using this assay.

E) Retinoid Modulation of Lipid Accumulation in C3H/10T1/2 Cells Stained with Oil Red O To further assess the retinoid regulation of adipocyte function we examined C3H/10T1/2 cells, which are mouse embryo fibroblast/multipotent stem cells that can be induced to differentiate into adipocytes or muscle cells. Table 2 shows the percent of C3H/10T1/2 cells that have differentiated into adipocytes as observed by oil red O staining assay. Experiment A was conducted in the presence of BRL 49653. Experiment B was conducted in the presence of both BRL 49653 and insulin. ALRT 1057 and LGD 1069 were used at 1 μM and TTNPB (RAR selective compound) was used at 10 nM concentration. Insulin was used at 0.01 mg/ml; and BRL 49653 was used at 0.1, 1 and 10 μM. C3H/10T1/2 cells were treated for 7 days, cells were stained with oil red O and observed under the microscope.

Morphological changes were observed when the cells were treated with retinoids alone, even though the cells did not fully differentiate into adipocytes. BRL 49653 alone caused no more than 10 percent of the cells to undergo adipocyte differentiation. However, when BRL 49653 was used in combination with an RXR agonist, LGD 1069 or ALRT 1057, there was a large increase in the amount of differentiation, the same effect was seen when BRL 49653 was used in combination with insulin.

The RAR agonist, TTNPB (which does not activate RXR), did not have the same effect as RXR agonist LGD 1069 and ALRT 1057. In fact, TTNPB inhibited the differentiation induced by BRL 49653 or BRL/insulin.

The above experiments show that a thiazolidinedione (BRL 49653) alone induces a minimal amount of differentiation in C3H/10T1/2 cells. However, when BRL 49653 is used in combination with a retinoid such as LG 100268, LGD 1069, or ALRT 1057, which are RXR agonists, differentiation is dramatically increased. This is not seen with the pure RAR agonist, TTNPB. These data support that the PPARγ/RXR heterodimers, which drive the adipocyte differentiation process, can be activated and enhanced by the binding of an RXR agonist. RXR agonists are useful for modulating the levels of glucose and triglyceride uptake.

Using RXR agonists to lower levels of glucose and triglycerides in animal models of NIDDM (A) In vivo experiment with db/db mice Animals: Strain Diabetic C57BLKS/J-m +/+db, 82 mice Source: Jackson Lab Stock number 000642

Genotype m+/+db xm +/+db

DOB Jun. 19, 1996±3d, DOA Jul. 23, 1996—34d old

Date of study: Aug. 5, 1996–Aug. 21, 1996, 44–63 d old

Mice were identified by an ear punch code (#1–82) and separated into 8 groups (A–H). Each group consisted of 10 mice separated into 4 cages with 2–3 mice/cage. Several mice were lost during the course of the study from fluid injections into the lungs resulting in 2 groups with 9 mice/group. Control group C consisted of 12 mice. The mice were fed pelleted Purina Lab chow #5015 containing 3.83 kcal/g with a caloric composition of 56% carbohydrate, 260 fat and 18% protein. Food and water were provided ad libitum. Food intake/cage was measured over selected periods and expressed as g food consumed/100 g mouse/day.

On days of study, food was removed from the cages at selected intervals of time between 6:15 and 7:00 AM. Animal weights were recorded 2 h after start of fast and blood samples taken after a 3 h fast. Blood was drawn from a cut at the tip of the tail and collected into a heparinized capillary tube (approx. 75 μl volume). After centrifugation, the hematocrit was read in a microcapillary reader, recorded and the tube broken for recovery of plasma for analysis of glucose, triglyceride and insulin concentration.

Blood samples were collected on days $0_{-1}$, 0, 3, 7, 10, and on the final day of study, days 13–15. After collection of blood samples on day 0, animals were refed their Purina chow diet and subsequently gavaged with control solution in group C and one of seven test solutions in groups designated A, B, D–H. The volume administered was equivalent in each group averaging 0.6 ml/42 g mouse (0.01429 ml/g). The various solutions were gavaged daily to their respective groups based on the animals weight taken that morning or the weight of the animal taken on the preceding day of weighing. To assess alterations in plasma FFA, on day 10 an addition 75 μl blood sample was collected into an EDTA-coated capillary tube immediately after collecting the basal heparinized capillary tube sample.

On the final day of study, mice were not gavaged with test solution. The last gavage was administered on the day preceding the final day, i.e., day 12 for animals terminated on day 13, day 13 for animals terminated on day 14 and day 14 for animals terminated on day 15. Terminal blood was collected by decapitation to provide serum for assessment of HDL.

Results

Figure 3:
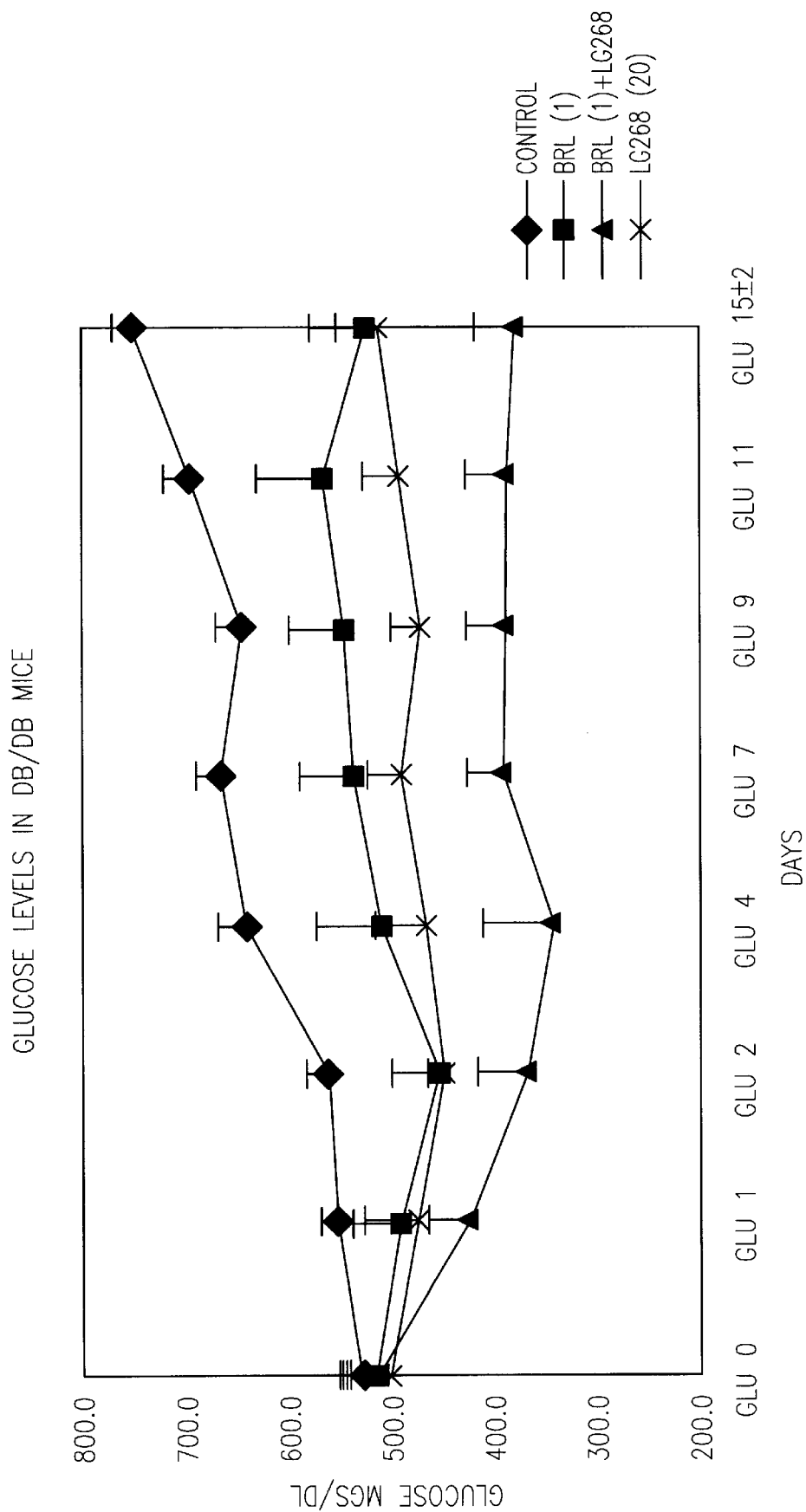
FIG. 3 is a graph showing the level of glucose in db/db mice treated with LG 100268, BRL 49653, and a combination of LG 100268 and BRL 49653, respectively.

FIG. 3 shows that BRL49653 and LG100268 each independently lowered the level of glucose in db/db mice. In addition, the combination of BRL49653 and LG100268 lowered the glucose level more than each compound did by itself. BRL 49653 (1 mg/kg) and LG 100268 (20 mg/kg) lowered the level of glucose by 40% by day 15 in comparison to control. The thiazolidinedione BRL 49653 at 1 mg/kg showed similar efficacy. The combination of an RXR activator and a PPAR activator showed greater efficacy, leading to almost 50% drop in the level of glucose. The effect of the combination was rapid, glucose levels were reduced by day 1 of the study and reached a steady state by day 4. This indicates a rapid resetting of the steady state levels of glucose homeostasis. Therefore, RXR activators enhance the efficacy of PPARγ activators, and vice vesa.

Figure 4:
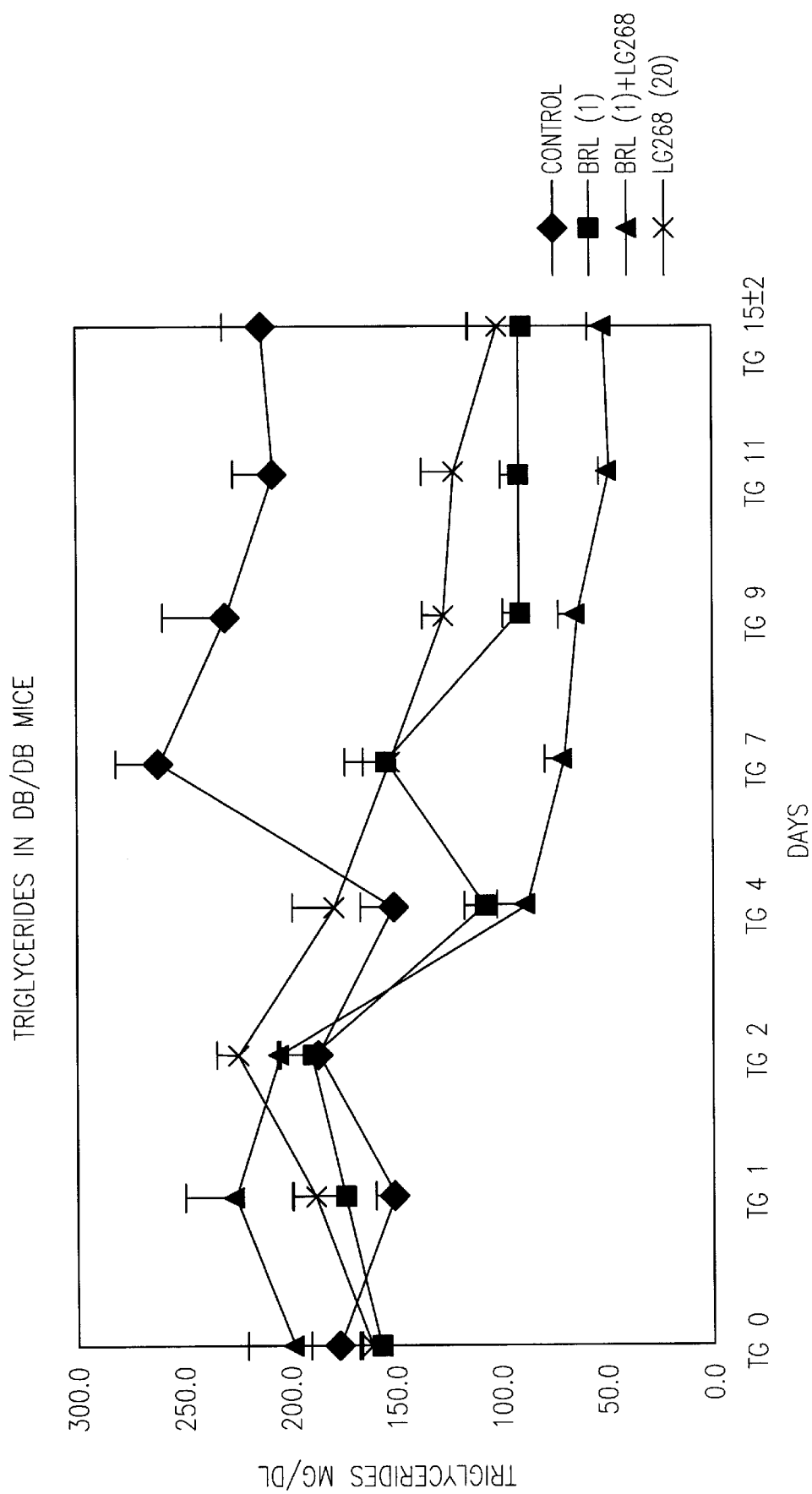
FIG. 4 is a graph showing the level of triglycerides in db/db mice treated with LG 100268, BRL 49653, and a combination of LG 100268 and BRL 49653, respectively.

FIG. 4 shows that RXR activators lowered the level of triglycerides in db/db mice. LG 100268 (20 mg/kg) lowered the level of triglycerides 40% by day 15 of the study. BRL 49653 (1 mg/kg) showed similar efficacy. The combination of these two compounds worked even better.

Figure 5:
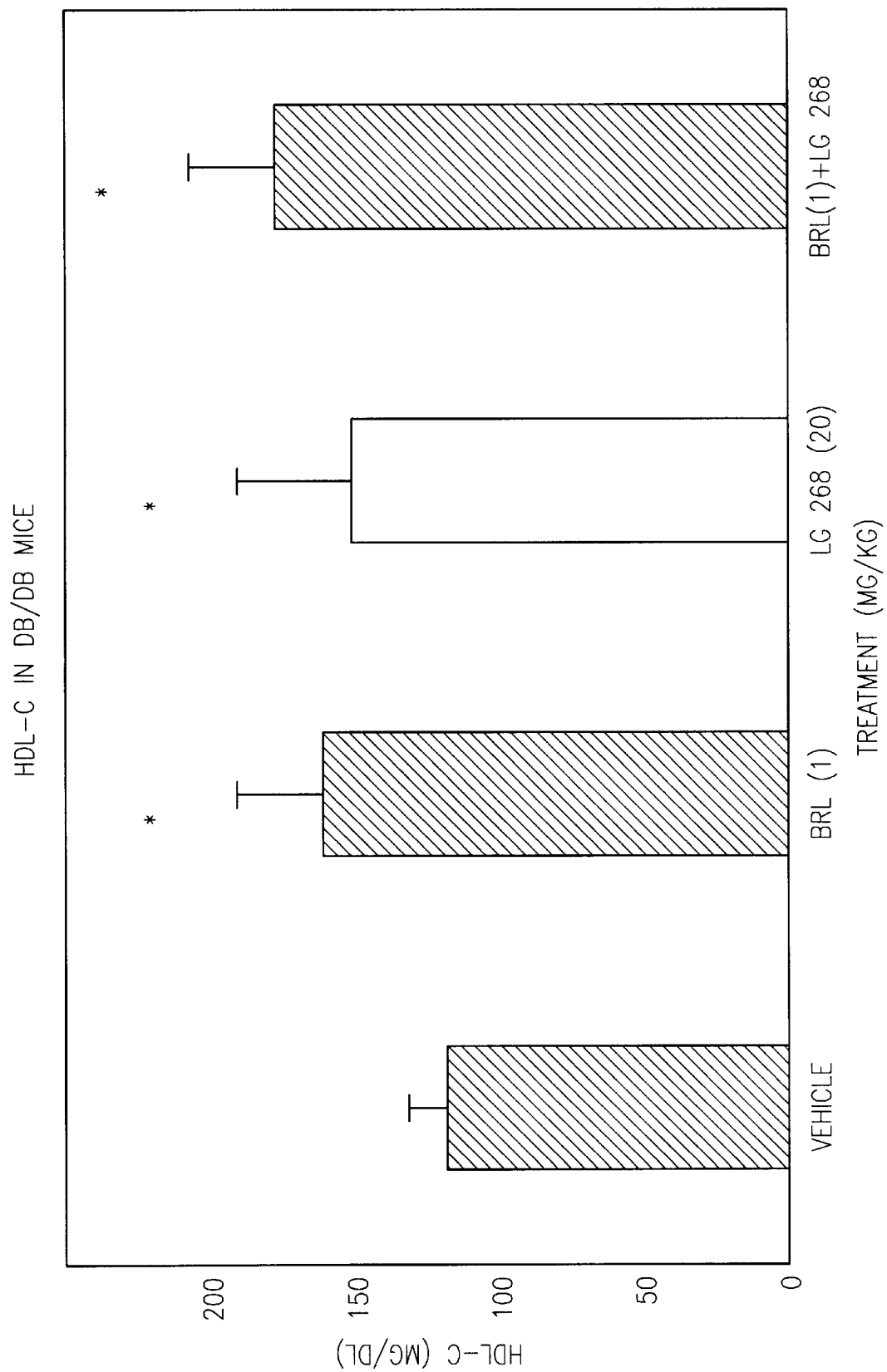
FIG. 5 is a graph showing the level of HDL cholesterol in db/db mice treated with LG 100268, BRL 49653, and a combination of LG 100268 and BRL 49653, respectively.

FIG. 5 shows that RXR activators modulators increased the level of HDL cholesterol in db/db mice. LG 100268 (20 mg/kg) increased HDL-cholesterol levels (20%) in comparison to controls in db/db mice. BRL 49653 caused an equivalent level of increase. The combination of these two compounds showed a higher increase. HDL-C was measured by the precipitation method using kits obtained from Bohringer-Mannheim (catalog #543004 and 427578).

(B) In vivo experiment with ob/ob mice

Animals: Strain Obese C57 BL/6J-Lep$^{ob(4)}$, 121 mice

Source: Jackson Lab Stock number 000632

Genotype Lep$^{ob(4)}$/+x Lep$^{ob(4)}$/+

DOB May 22, 1996±3 d, DOA Jul. 2, 1996—41d old

Date of study: Jul. 21, 1996–Aug. 2, 1996—49–70d old

Mice were identified by an ear punch code (#1–121) and separated into 12 groups. Each group consisting of 10 mice. (one mouse was terminated before start of the study because of bad teeth causing initial weight loss. As in preceding studies, mice in each group were housed in 4 cages (2–3 mice/cage) and provided water and Purina Lab chow #505/15 ad libitum.

On days of study, food was removed from the cages at selected intervals of time between 6:15 and 7:00 AM. Animal weights were recorded 2 h after start of fast and blood samples taken after a 3 h fast. Blood was drawn from a cut at the tip of the tail and collected into a heparinized capillary tube (approx. 75 µl volume). After centrifugation, the hematocrit was read in a microcapillary reader, recorded and the tube broken for recovery of plasma for analysis of glucose, triglyceride and insulin concentration.

Blood samples were collected on days $0_{-3}$, 0, 3, 6, 8, 10, 14±1 and final collections were made on days 15, 16 or 17. FFA samples were collected on day 10 by drawing a second 75 µl blood sample in a non-heparinized tube coated with EDTA. This tube was collected immediately after the heparinized tube collection.

Animals in groups H were administered control gavage solution (0.6 ml/42 g) daily commencing on day 0 and ending on the day preceding the final day. 11 test solutions were administered to animals in groups designated A–G, I–L. All gavage solutions were administered after refeeding on days in which mice were fasted for blood sampling.

Results

Figure 6:
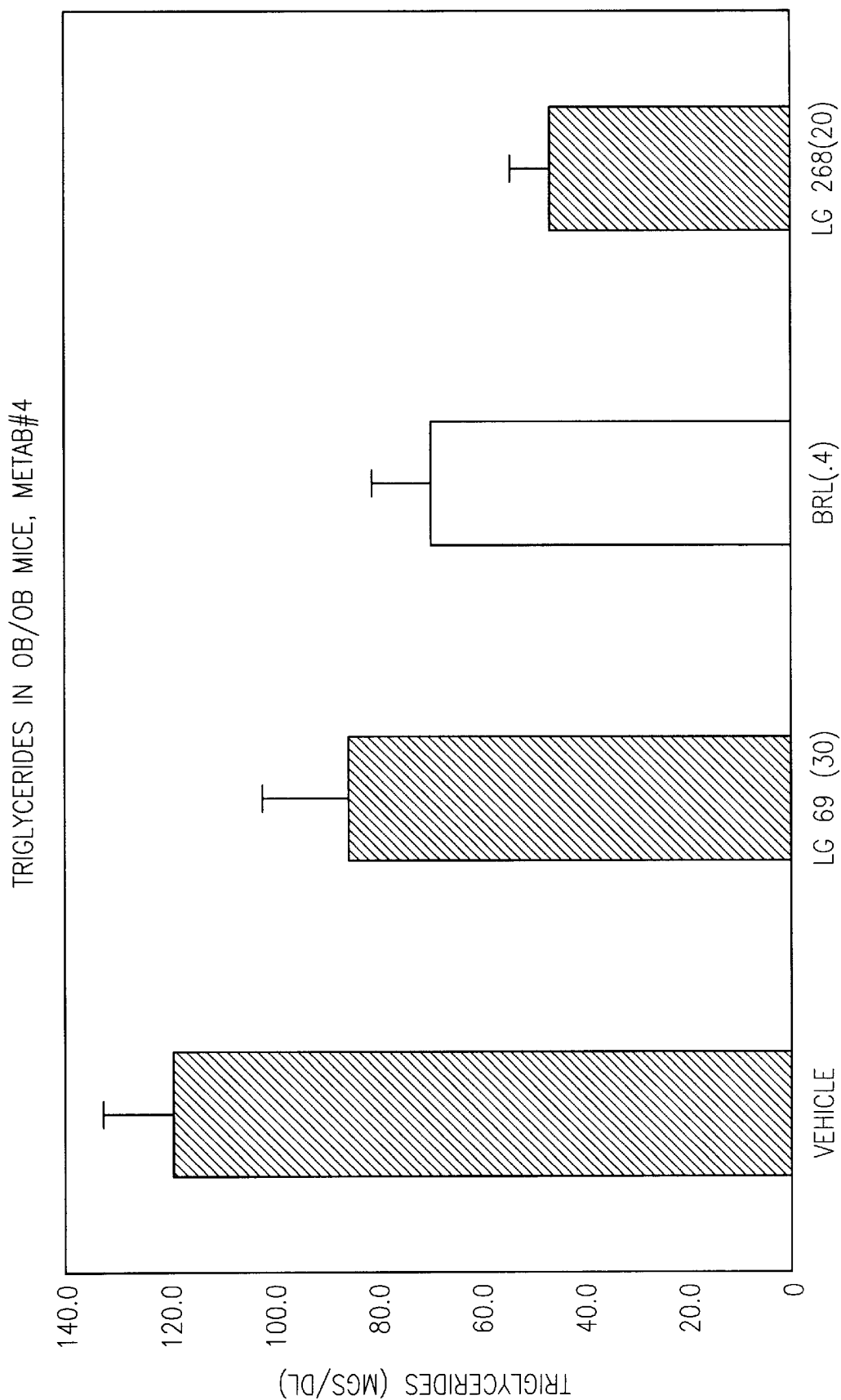
FIG. 6 is a graph showing the level of triglycerides in ob/ob mice treated with LGD 1069, LG 100268, and BRL 49653, respectively.

FIG. 6 shows that RXR modulators lowered the level of triglycerides in ob/ob mice. RXR activators LGD 1069 (30 mg/kg) and LG 100268 (20 mg/kg) lowered the level of triglycerides by 34% and 60% respectively in ob/ob mice by day 14 of the study. BRL 49653 was also able to lower the level of triglycerides, although not as efficacious as LG100268.

Figure 7:
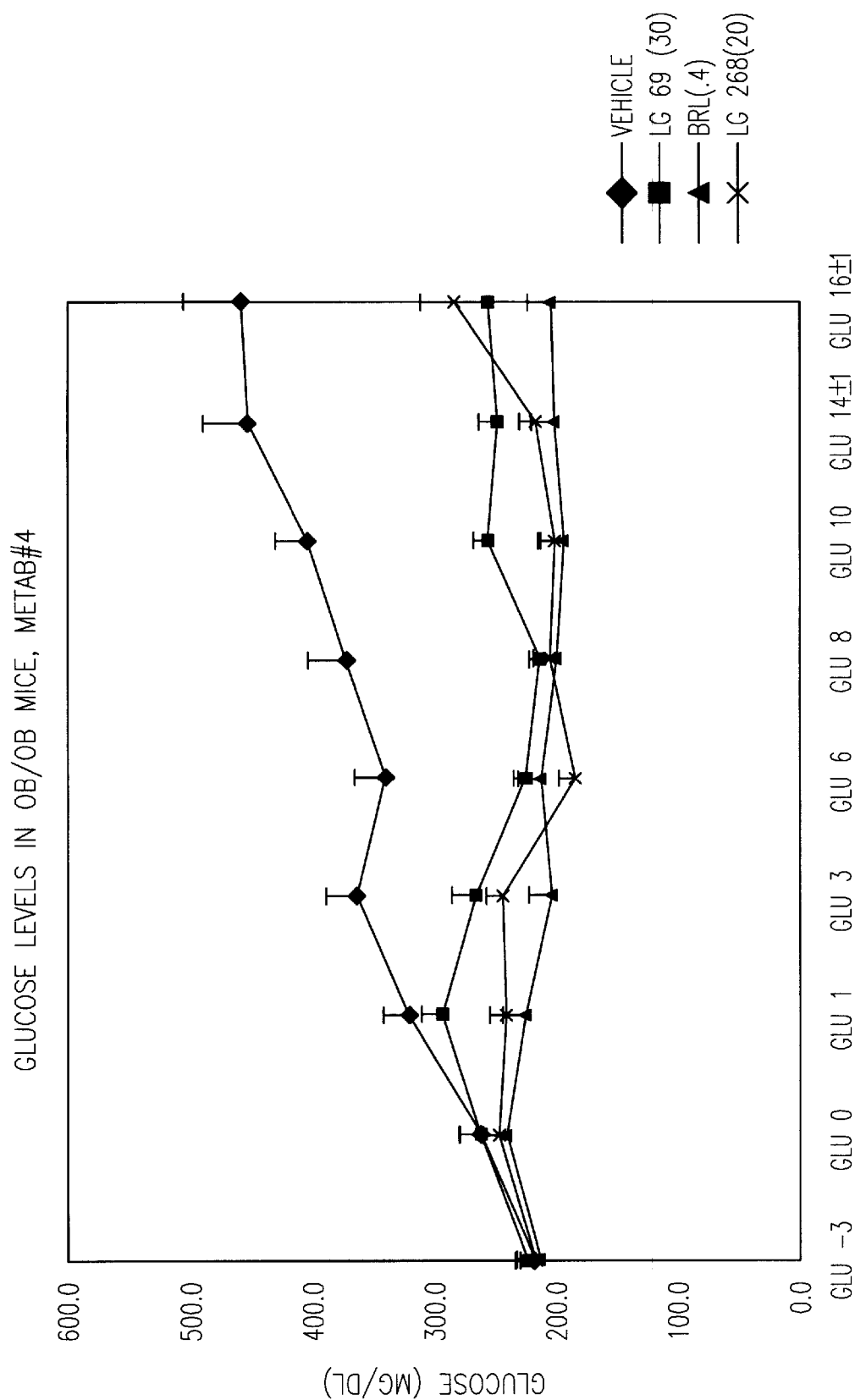
FIG. 7 is a graph showing the level of glucose in ob/ob mice treated with LGD 1069, LG 100268, and BRL 49653, respectively.

FIG. 7 shows that RXR modulators lowered the level of glucose in ob/ob mice. RXR activators LGD 1069 at 30 mg/kg and LG 100268 at 20 mg/kg lowered the level of glucose nearly 50% in comparison to control. The level of glucose was reduced to almost euglycemic levels by day 14 of the study. BRL 49653 (0.4 mg/kg) showed similar efficacy.

Figure 8:
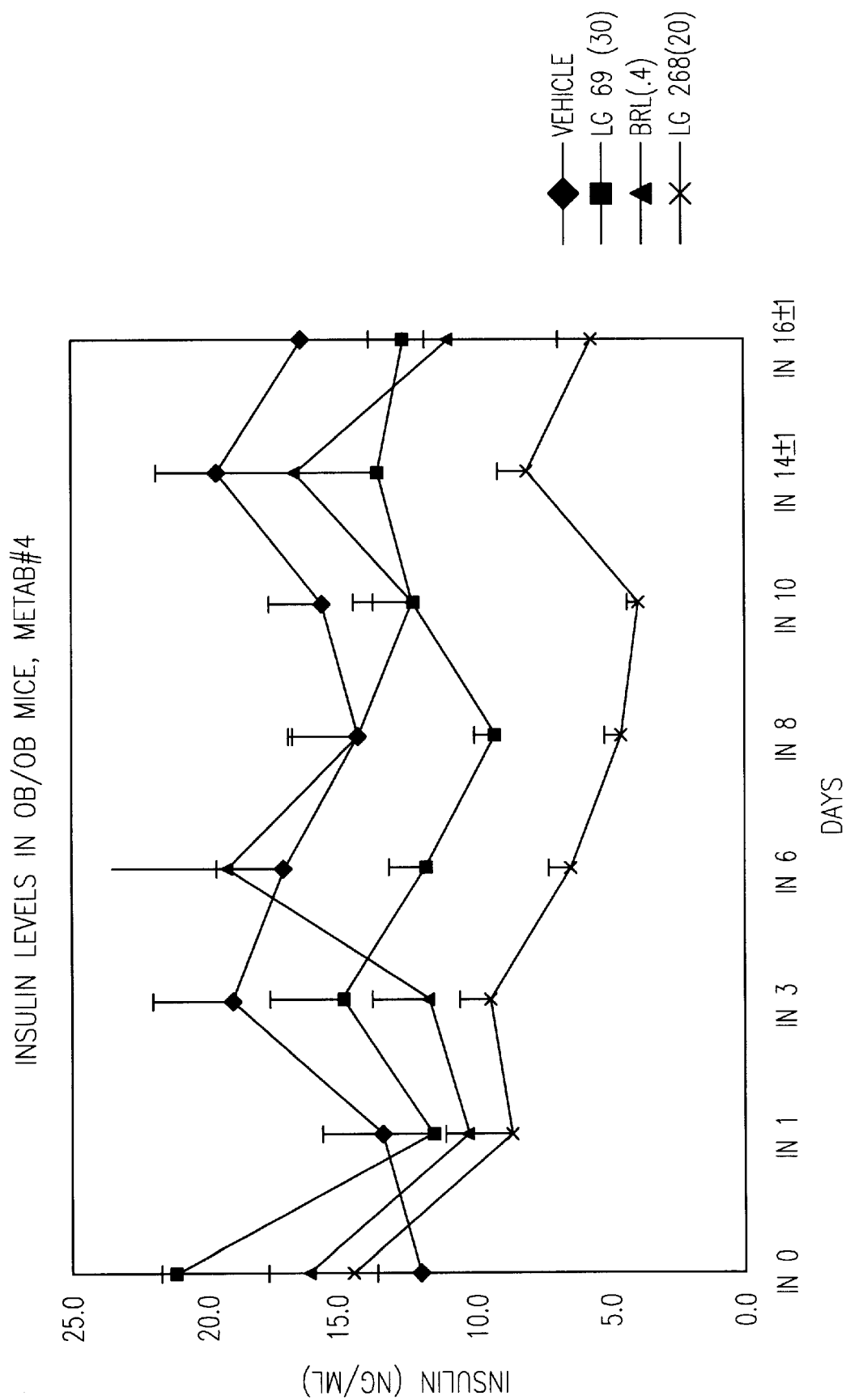
FIG. 8 is a graph showing the level of insulin in ob/ob mice treated with LGD 1069, LG 100268, and BRL 49653, respectively.

FIG. 8 shows that RXR modulators, LGD 1069 (30 mg/kg) and LG 100268 (20 mg/kg), lowered the level of insulin in ob/ob mice. LG100268 lowered the level of insulin by 66% by day 14 of the study. LGD 1069 showed lower efficacy. There was a very rapid effect of the compounds since the level of insulin started to drop in day 1.

Pharmaceutical Formulations and Modes of Administration

The particular compound that affects the disorders or conditions of interest can be administered to a patient either by themselves, or in pharmaceutical compositions where it is mixed with suitable carriers or excipient(s). In treating a patient exhibiting a disorder of interest, a therapeutically effective amount of a agent or agents such as these is administered. A therapeutically effective dose refers to that amount of the compound that results in amelioration of symptoms or a prolongation of survival in a patient.

The compounds also can be prepared as pharmaceutically acceptable salts. Examples of pharmaceutically acceptable salts include acid addition salts such as those containing hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate. (See e.g., PCT/US92/03736). Such salts can be derived using acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid. These salts can be prepared by standard techniques. For example, the free base form of the compound is first dissolved in a suitable solvent such as an aqueous or aqueous-alcohol solution, containing the appropriate acid. The salt is then isolated by evaporating the solution. In another example, the salt is prepared by reacting the free base and acid in an organic solvent.

Carriers or excipients can be used to facilitate administration of the compound, for example, to increase the solubility of the compound. Examples of carriers and excipients include calcium carbonate, calcium phosphate, various sugars or types of starch, cellulose derivatives, gelatin, vegetable oils, polyethylene glycols and physiologically compatible solvents.

In addition, the molecules tested can be used to determine the structural features that enable them to act on the RXR/PPARγ heterodimer, and thus to select molecules useful in this invention. Those skilled in the art will know how to design drugs from lead molecules, using techniques such as those disclosed in PCT publication WO 94/18959, incorporated by reference herein.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. Levels in plasma may be measured, for example, by HPLC.

The exact formulation, route of administration and dosage can be chosen by the individual physician in view of the patient's condition. (See e.g. Fingl et al., in *The Pharma-* cological Basis of Therapeutics, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in *Remington's Pharmaceutical Sciences*, 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Liposomes may be used for encapsulated delivery.

Pharmaceutical formulations disclosed or described in Boehm, et al., WO94/15902 are incorporated by reference herein.

All publications referenced are incorporated by reference herein, including the nucleic acid sequences and amino acid sequences listed in each publication. All the compounds disclosed and referred to in the publications mentioned above are incorporated by reference herein, including those compounds disclosed and referred to in articles cited by the publications mentioned above.

Other embodiments of this invention are disclosed in the following claims.

TABLE 1

Oil Red O Staining in 3T3-L1 Differentiating Adipocytes

| Treatment | Percent of Differentiated Cells |
| --- | --- |
| Control | 0.1 |
| BRL 49653 | 50 |
| Insulin | 20 |
| LG 100268 | 50 |
| BRL + Insulin | 80 |
| BRL + LG 100268 | 90 |
| LG 100268 + Insulin | 90 |

TABLE 2

Retinoid Modulation of Adipocyte differentiation in C3H/10T1/2 Cells

| Treatment | Experiment A (+ BRL) % differentiated cells | Experiment B (+ BRL + Insulin) % differentiated cells |
| --- | --- | --- |
| BRL (10 µM) | 10 | 80 |
| BRL (1 µM) | 8 | 80 |
| BRL (0.1 µM) | 5 | 60 |
| BRL (10 µM) | 10 | 80 |
| + ALRT 1057 (1 µM) | 80 | 99 |
| + LGD 1069 (1 µM) | 80 | 99 |
| + TTNPB (10nM) | 5 | 50 |
| BRL (1 µM) | 8 | 80 |
| + ALRT 1057 (1 µM) | 65 | 90 |
| + LGD 1069 (1 µM) | 65 | 90 |
| + TTNPB (10 nM) | 2 | 30 |
| BRL (0.1 µM) | 5 | 60 |
| + ALRT 1057 (1 µM) | 45 | 85 |
| + LGD 1069 (1 µM) | 45 | 90 |
| + TTNPB (10 nM) | 0.2 | |

Undifferentiated controls 0% differentiation.

What is claimed is:

1. Method for increasing glucose uptake in adipose or muscle tissue, comprising the step of administering to said tissue a composition comprising a pharmaceutically effective amount of an RXR agonist.

2. The method of claim 1, further comprising the step of administering to said tissue a composition comprising a pharmaceutically effective amount of a PPARγ agonist.

3. The method of claim 1, wherein said composition further comprises a pharmaceutically effective amount of a PPARγ agonist.

4. The method of claim 1, wherein said RXR agonist is an RXR specific agonist.

5. The method of claim 4, wherein said RXR agonist is LG 100268.

6. The method of claim 4, wherein said RXR agonist is LGD 1069.

7. The method of claim 1, wherein said RXR agonist also activates a retinoic acid receptor.

8. The method of claim 7, wherein said RXR agonist is 9-cis retinoic acid.

9. The method of claim 2, wherein said PPARγ agonist is a thiazolidinedione compound.

10. The method of claim 9, wherein said thiazolidinedione compound is selected from the group consisting of BRL 49653, troglitazone, pioglitazone, ciglitazone, WAY-120,744, englitazone, AD 5075 and darglitazone.

11. The method of claim 1, further comprising the step of administering to said tissue a composition comprising a pharmaceutically effective amount of insulin, insulin derivative, insulin secretagogue, insulin sensitizer or insulin mimetic.

12. The method of claim 3, wherein said composition further contains a pharmaceutically effective amount of insulin, insulin mimetic, or insulin sensitizer.

13. A method of treating non-insulin-dependent diabetes mellitus in a host suffering therefrom, comprising the step of administering to said host a pharmaceutically effective amount of an RXR agonist.

14. The method of claim 13, wherein said RXR agonist is an RXR specific agonist.

15. The method of claim 14, wherein said RXR specific agonist is 2-[1-(3,5,5,8,8-pentamethyl-5,6,7,8-tetrahydro-2-naphthyl)-cyclopropyl]-pyridine-5-carboxylic acid or a pharmaceutically acceptable salt thereof.

16. The method of claim 14, wherein said RXR specific agonist is 4-[(3,5,5,8,8-pentamethyl-5,6,7,8-tetrahydro-2-naphthyl) 2-carbonyl]-benzoic acid or a pharmaceutically acceptable salt thereof.

17. The method of claim 13, further comprising the step of administering to said host a pharmaceutically effective amount of a PPARγ agonist.

18. The method of claim 17, wherein said PPARγ agonist is a thiazolidinedione compound.

19. The method of claim 18, wherein said thiazolidinedione compound is selected from the group consisting of 5-[[4-[2-(methyl-2-pyridinylamino)ethoxy]phenyl]methyl]-2,4-thiazolidinedione, troglitazone, pioglitazone, ciglitazone, WAY-120,744, englitazone, AD 5075, darglitazone, and their pharmaceutically acceptable salts.

20. The method of claim 13, further comprising the step of administering to said host a pharmaceutically effective amount of a compound selected from the group consisting of insulin, an insulin derivative, an insulin secretagogue, an insulin sensitizer, and an insulin mimetic.

21. The method of claim 17, further comprising the step of administering to said host a pharmaceutically effective amount of a compound selected from the group consisting of insulin, an insulin derivative, an insulin secretagogue, an insulin sensitizer, and an insulin mimetic.

22. The method of claim 13, wherein said RXR agonist is orally, topically, intravenously, transdermally, rectally, or parentally administered to said host.

23. The method of claim 13, wherein said RXR agonist is administered to said host in a pharmaceutical composition comprising a pharmaceutically acceptable carrier or excipient.

24. The method of claim 17, wherein said RXR agonist and said PPARγ agonist are administered to said host in a pharmaceutical composition comprising a pharmaceutically acceptable carrier or excipient.

25. The method of claim 20, wherein said RXR agonist and said compound are administered to said host in a pharmaceutical composition comprising a pharmaceutically acceptable carrier or excipient.

26. The method of claim 21, wherein said RXR agonist, said PPARγ agonist and said compound are administered to said host in a pharmaceutical composition comprising a pharmaceutically acceptable carrier or excipient.

27. The method of claim 23, 24, 25 or 26, wherein said pharmaceutical composition consists of a single dosage unit.

28. A method of increasing glucose uptake in the adipose or muscle tissue of a host, comprising the step of administering to said host a pharmaceutically effective amount of an RXR agonist.

29. The method of claim 28, wherein said RXR agonist is an RXR specific agonist.

30. The method of claim 29, wherein said RXR specific agonist is 2-[1-(3,5,5,8,8-pentamethyl-5,6,7,8-tetrahydro-2-naphthyl)-cyclopropyl]-pyridine-5-carboxylic acid or a pharmaceutically acceptable salt thereof.

31. The method of claim 29, wherein said RXR specific agonist is 4-[(3,5,5,8,8-pentamethyl-5,6,7,8-tetrahydro-2-naphthyl)-2-carbonyl]-benzoic acid or a pharmaceutically acceptable salt thereof.

32. The method of claim 28, further comprising the step of administering to said host a pharmaceutically effective amount of a PPARγ agonist.

33. The method of claim 32, wherein said PPARγ agonist is a thiazolidinedione compound.

34. The method of claim 33, wherein said thiazolidinedione compound is selected from the group consisting of 5-[[4-[2-(methyl-2-pyridinylamino)ethoxy]phenyl]methyl]-2,4-thiazolidinedione, troglitazone, pioglitazone, ciglitazone, WAY-120,744, englitazone, AD 5075, darglitazone, and their pharmaceutically acceptable salts.

35. The method of claim 28, further comprising the step of administering to said host a pharmaceutically effective amount of a compound selected from the group consisting of insulin, an insulin derivative, an insulin secretagogue, an insulin sensitizer, and an insulin mimetic.

36. The method of claim 32, further comprising the step of administering to said host a pharmaceutically effective amount of a compound selected from the group consisting of insulin, an insulin derivative, an insulin secretagogue, an insulin sensitizer, and an insulin mimetic.

37. The method of claim 28, wherein said RXR agonist is orally, topically, intravenously, transdermally, rectally, or parentally administered to said host.

38. The method of claim 28, wherein said RXR agonist is administered to said host in a pharmaceutical composition comprising a pharmaceutically acceptable carrier or excipient.

39. The method of claim 32, wherein said RXR agonist and said PPARγ agonist are administered to said host in a pharmaceutical composition comprising a pharmaceutically acceptable carrier or excipient.

40. The method of claim 35, wherein said RXR agonist and said compound are administered to said host in a pharmaceutical composition comprising a pharmaceutically acceptable carrier or excipient.

41. The method of claim 36, wherein said RXR agonist, said PPARγ agonist and said compound are administered to said host in a pharmaceutical composition comprising a pharmaceutically acceptable carrier or excipient.

42. The method of claim 38, 39, 40 or 41, wherein said pharmaceutical composition consists of a single dosage unit.

43. A method of treating hyperglycemia in a host suffering therefrom, comprising the step of administering to said host a pharmaceutically effective amount of an RXR agonist.

44. The method of claim 43, wherein said RXR agonist is an RXR specific agonist.

45. The method of claim 44, wherein said RXR specific agonist is 2-[1-(3,5,5,8,8-pentamethyl-5,6,7,8-tetrahydro-2-naphthyl)-cyclopropyl]-pyridine-5-carboxylic acid or a pharmaceutically acceptable salt thereof.

46. The method of claim 44, wherein said RXR specific agonist is 4-[(3,5,5,8,8-pentamethyl-5,6,7,8-tetrahydro-2-naphthyl)- 2-carbonyl]-benzoic acid or a pharmaceutically acceptable salt thereof.

47. The method of claim 43, further comprising the step of administering to said host a pharmaceutically effective amount of a PPARγ agonist.

48. The method of claim 47, wherein said PPARγ agonist is a thiazolidinedione compound.

49. The method of claim 48, wherein said thiazolidinedione compound is selected from the group consisting of 5-[[4-[2-(methyl-2-pyridinylamino)ethoxy]phenyl]methyl]-2,4-thiazolidinedione, troglitazone, pioglitazone, ciglitazone, WAY-120,744, englitazone, AD 5075, darglitazone, and their pharmaceutically acceptable salts.

50. The method of claim 43, further comprising the step of administering to said host a pharmaceutically effective amount of a compound selected from the group consisting of insulin, an insulin derivative, an insulin secretagogue, an insulin sensitizer, and an insulin mimetic.

51. The method of claim 47, further comprising the step of administering to said host a pharmaceutically effective amount of a compound selected from the group consisting of insulin, an insulin derivative, an insulin secretagogue, an insulin sensitizer, and an insulin mimetic.

52. The method of claim 43, wherein said RXR agonist is orally, topically, intravenously, transdermally, rectally, or parentally administered to said host.

53. The method of claim 43, wherein said RXR agonist is administered to said host in a pharmaceutical composition comprising a pharmaceutically acceptable carrier or excipient.

54. The method of claim 47, wherein said RXR agonist and said PPARγ agonist are administered to said host in a pharmaceutical composition comprising a pharmaceutically acceptable carrier or excipient.

55. The method of claim 50, wherein said RXR agonist and said compound are administered to said host in a pharmaceutical composition comprising a pharmaceutically acceptable carrier or excipient.

56. The method of claim 51, wherein said RXR agonist, said PPARγ agonist and said compound are administered to said host in a pharmaceutical composition comprising a pharmaceutically acceptable carrier or excipient.

57. The method of claim 53, 54, 55 or 56, wherein said pharmaceutical composition consists of a single dosage unit.

58. A method of treating hyperinsulinemia in a host suffering therefrom, comprising the step of administering to said host a pharmaceutically effective amount of an RXR agonist.

59. The method of claim 58, wherein said RXR agonist is an RXR specific agonist.

60. The method of claim 59, wherein said RXR specific agonist is 2-[1-(3,5,5,8,8-pentamethyl-5,6,7,8-tetrahydro-2-naphthyl)-cyclopropyl]-pyridine-5-carboxylic acid or a pharmaceutically acceptable salt thereof.

61. The method of claim 59, wherein said RXR specific agonist is 4-[(3,5,5,8,8-pentamethyl-5,6,7,8-tetrahydro-2-naphthyl)-2-carbonyl]-benzoic acid or a pharmaceutically acceptable salt thereof.

62. The method of claim 58, further comprising the step of administering to said host a pharmaceutically effective amount of a PPARγ agonist.

63. The method of claim 62, wherein said PPARγ agonist is a thiazolidinedione compound.

64. The method of claim 63, wherein said thiazolidinedione compound is selected from the group consisting of 5-[[4-[2-(methyl-2-pyridinylamino)ethoxy]phenyl]methyl]-2,4-thiazolidinedione, troglitazone, pioglitazone, ciglitazone, WAY-120,744, englitazone, AD 5075, darglitazone, and their pharmaceutically acceptable salts.

65. The method of claim 58, further comprising the step of administering to said host a pharmaceutically effective amount of a compound selected from the group consisting of insulin, an insulin derivative, an insulin secretagogue, an insulin sensitizer, and an insulin mimetic.

66. The method of claim 62, further comprising the step of administering to said host a pharmaceutically effective amount of a compound selected from the group consisting of insulin, an insulin derivative, an insulin secretagogue, an insulin sensitizer, and an insulin mimetic.

67. The method of claim 58, wherein said RXR agonist is orally, topically, intravenously, transdermally, rectally, or parentally administered to said host.

68. The method of claim 58, wherein said RXR agonist is administered to said host in a pharmaceutical composition comprising a pharmaceutically acceptable carrier or excipient.

69. The method of claim 62, wherein said RXR agonist and said PPARγ agonist are administered to said host in a pharmaceutical composition comprising a pharmaceutically acceptable carrier or excipient.

70. The method of claim 65, wherein said RXR agonist and said compound are administered to said host in a pharmaceutical composition comprising a pharmaceutically acceptable carrier or excipient.

71. The method of claim 66, wherein said RXR agonist, said PPARγ agonist and said compound are administered to said host in a pharmaceutical composition comprising a pharmaceutically acceptable carrier or excipient.

72. The method of claim 68, 69, 70 or 71, wherein said pharmaceutical composition consists of a single dosage unit.

73. A method of increasing insulin sensitivity in a host in need thereof, comprising the step of administering to said host a pharmaceutically effective amount of an RXR agonist.

74. The method of claim 73, wherein said RXR agonist is an RXR specific agonist.

75. The method of claim 74, wherein said RXR specific agonist is 2-[1-(3,5,5,8,8-pentamethyl-5,6,7,8-tetrahydro-2-naphthyl)-cyclopropyl]-pyridine-5-carboxylic acid or a pharmaceutically acceptable salt thereof.

76. The method of claim 74, wherein said RXR specific agonist is 4-[(3,5,5,8,8-pentamethyl-5,6,7,8-tetrahydro-2-naphthyl)- 2-carbonyl]-benzoic acid or a pharmaceutically acceptable salt thereof.

77. The method of claim 73, further comprising the step of administering to said host a pharmaceutically effective amount of a PPARγ agonist.

78. The method of claim 77, wherein said PPARγ agonist is a thiazolidinedione compound.

79. The method of claim 78, wherein said thiazolidinedione compound is selected from the group consisting of 5-[[4-[2-(methyl-2-pyridinylamino)ethoxy]phenyl]methyl]-2,4-thiazolidinedione, troglitazone, pioglitazone, ciglitazone, WAY-120,744, englitazone, AD 5075, darglitazone, and their pharmaceutically acceptable salts.

80. The method of claim 73, further comprising the step of administering to said host a pharmaceutically effective amount of a compound selected from the group consisting of insulin, an insulin derivative, an insulin secretagogue, an insulin sensitizer, and an insulin mimetic.

81. The method of claim 77, further comprising the step of administering to said host a pharmaceutically effective amount of a compound selected from the group consisting of insulin, an insulin derivative, an insulin secretagogue, an insulin sensitizer, and an insulin mimetic.

82. The method of claim 73, wherein said RXR agonist is orally, topically, intravenously, transdermally, rectally, or parentally administered to said host.

83. The method of claim 73, wherein said RXR agonist is administered to said host in a pharmaceutical composition comprising a pharmaceutically acceptable carrier or excipient.

84. The method of claim 77, wherein said RXR agonist and said PPARγ agonist are administered to said host in a pharmaceutical composition comprising a pharmaceutically acceptable carrier or excipient.

85. The method of claim 80, wherein said RXR agonist and said compound are administered to said host in a pharmaceutical composition comprising a pharmaceutically acceptable carrier or excipient.

86. The method of claim 81, wherein said RXR agonist, said PPARγ agonist and said compound are administered to said host in a pharmaceutical composition comprising a pharmaceutically acceptable carrier or excipient.

87. The method of claim 83, 84, 85 or 86, wherein said pharmaceutical composition consists of a single dosage unit.

88. A method of preventing insulin resistance in a host with propensity thereof, comprising the step of administering to said host a pharmaceutically effective amount of an RXR agonist.

89. The method of claim 88, wherein said RXR agonist is an RXR specific agonist.

90. The method of claim 89, wherein said RXR specific agonist is 2-[1-(3,5,5,8,8-pentamethyl-5,6,7,8-tetrahydro-2-naphthyl)-cyclopropyl]-pyridine-5-carboxylic acid or a pharmaceutically acceptable salt thereof.

91. The method of claim 89, wherein said RXR specific agonist is 4-[(3,5,5,8,8-pentamethyl-5,6,7,8-tetrahydro-2-naphthyl)-2-carbonyl]-benzoic acid or a pharmaceutically acceptable salt thereof.

92. The method of claim 88, further comprising the step of administering to said host a pharmaceutically effective amount of a PPARγ agonist.

93. The method of claim 92, wherein said PPARγ agonist is a thiazolidinedione compound.

94. The method of claim 93, wherein said thiazolidinedione compound is selected from the group consisting of 5-[[4-[2-(methyl-2-pyridinylamino)ethoxy]phenyl]methyl]-2,4-thiazolidinedione, troglitazone, pioglitazone, ciglitazone, WAY-120,744, englitazone, AD 5075, darglitazone, and their pharmaceutically acceptable salts.

95. The method of claim 88, further comprising the step of administering to said host a pharmaceutically effective amount of a compound selected from the group consisting of insulin, an insulin derivative, an insulin secretagogue, an insulin sensitizer, and an insulin mimetic.

96. The method of claim 92, further comprising the step of administering to said host a pharmaceutically effective amount of a compound selected from the group consisting of insulin, an insulin derivative, an insulin secretagogue, an insulin sensitizer, and an insulin mimetic.

97. The method of claim 88, wherein said RXR agonist is orally, topically, intravenously, transdermally, rectally, or parentally administered to said host.

98. The method of claim 88, wherein said RXR agonist is administered to said host in a pharmaceutical composition comprising a pharmaceutically acceptable carrier or excipient.

99. The method of claim 92, wherein said RXR agonist and said PPARγ agonist are administered to said host in a pharmaceutical composition comprising a pharmaceutically acceptable carrier or excipient.

100. The method of claim 95, wherein said RXR agonist and said compound are administered to said host in a pharmaceutical composition comprising a pharmaceutically acceptable carrier or excipient.

101. The method of claim 96, wherein said RXR agonist, said PPARγ agonist and said compound are administered to said host in a pharmaceutical composition comprising a pharmaceutically acceptable carrier or excipient.

102. The method of claim 98, 99, 100 or 101, wherein said pharmaceutical composition consists of a single dosage unit.

103. A method of preventing or slowing the development of one or more symptoms of non-insulin-dependent diabetes mellitus in a host, comprising the step of administering to said host a pharmaceutically effective amount of an RXR agonist.

104. The method of claim 103, wherein said RXR agonist is an RXR specific agonist.

105. The method of claim 104, wherein said RXR specific agonist is 2-[1-(3,5,5,8,8-pentamethyl-5,6,7,8-tetrahydro-2-naphthyl)-cyclopropyl]-pyridine-5-carboxylic acid or a pharmaceutically acceptable salt thereof.

106. The method of claim 104, wherein said RXR specific agonist is 4-[(3,5,5,8,8-pentamethyl-5,6,7,8-tetrahydro-2-naphthyl)-2-carbonyl]-benzoic acid or a pharmaceutically acceptable salt thereof.

107. The method of claim 103, further comprising the step of administering to said host a pharmaceutically effective amount of a PPARγ agonist.

108. The method of claim 107, wherein said PPARγ agonist is a thiazolidinedione compound.

109. The method of claim 108, wherein said thiazolidinedione compound is selected from the group consisting of 5-[[4-[2-(methyl-2-pyridinylamino)ethoxy]phenyl]methyl]-2,4-thiazolidinedione, troglitazone, pioglitazone, ciglitazone, WAY-120,744, englitazone, AD 5075, darglitazone, and their pharmaceutically acceptable salts.

110. The method of claim 103, further comprising the step of administering to said host a pharmaceutically effective amount of a compound selected from the group consisting of insulin, an insulin derivative, an insulin secretagogue, an insulin sensitizer, and an insulin mimetic.

111. The method of claim 107, further comprising the step of administering to said host a pharmaceutically effective amount of a compound selected from the group consisting of insulin, an insulin derivative, an insulin secretagogue, an insulin sensitizer, and an insulin mimetic.

112. The method of claim 103, wherein said RXR agonist is orally, topically, intravenously, transdermally, rectally, or parentally administered to said host.

113. The method of claim 103, wherein said RXR agonist is administered to said host in a pharmaceutical composition comprising a pharmaceutically acceptable carrier or excipient.

114. The method of claim 107, wherein said RXR agonist and said PPARγ agonist are administered to said host in a pharmaceutical composition comprising a pharmaceutically acceptable carrier or excipient.

115. The method of claim 110, wherein said RXR agonist and said compound are administered to said host in a pharmaceutical composition comprising a pharmaceutically acceptable carrier or excipient.

116. The method of claim 111, wherein said RXR agonist, said PPARγ agonist and said compound are administered to said host in a pharmaceutical composition comprising a pharmaceutically acceptable carrier or excipient.

117. The method of claim 111, 114, 115 or 116, wherein said pharmaceutical composition consists of a single dosage unit.

118. A method of preventing hyperglycemia in a host with propensity thereof, comprising the step of administering to said host a pharmaceutically effective amount of an RXR agonist.

119. The method of claim 118, wherein said RXR agonist is an RXR specific agonist.

120. The method of claim 119, wherein said RXR specific agonist is 2-[1-(3,5,5,8,8-pentamethyl-5,6,7,8-tetrahydro-2-naphthyl)-cyclopropyl]-pyridine-5-carboxylic acid or a pharmaceutically acceptable salt thereof.

121. The method of claim 119, wherein said RXR specific agonist is 4-[(3,5,5,8,8-pentamethyl-5,6,7,8-tetrahydro-2-naphthyl)-2-carbonyl]-benzoic acid or a pharmaceutically acceptable salt thereof.

122. The method of claim 118, further comprising the step of administering to said host a pharmaceutically effective amount of a PPARγ agonist.

123. The method of claim 122, wherein said PPARγ agonist is a thiazolidinedione compound.

124. The method of claim 123, wherein said thiazolidinedione compound is selected from the group consisting of 5-[[4-[2-(methyl-2-pyridinylamino)ethoxy]phenyl]methyl]-2,4-thiazolidinedione, troglitazone, pioglitazone, ciglitazone, WAY-120,744, englitazone, AD 5075, darglitazone, and their pharmaceutically acceptable salts.

125. The method of claim 118, further comprising the step of administering to said host a pharmaceutically effective amount of a compound selected from the group consisting of insulin, an insulin derivative, an insulin secretagogue, an insulin sensitizer, and an insulin mimetic.

126. The method of claim 122, further comprising the step of administering to said host a pharmaceutically effective amount of a compound selected from the group consisting of insulin, an insulin derivative, an insulin secretagogue, an insulin sensitizer, and an insulin mimetic.

127. The method of claim 118, wherein said RXR agonist is orally, topically, intravenously, transdermally, rectally, or parentally administered to said host.

128. The method of claim 118, wherein said RXR agonist is administered to said host in a pharmaceutical composition comprising a pharmaceutically acceptable carrier or excipient.

129. The method of claim 122, wherein said RXR agonist and said PPARγ agonist are administered to said host in a pharmaceutical composition comprising a pharmaceutically acceptable carrier or excipient.

130. The method of claim 125, wherein said RXR agonist and said compound are administered to said host in a pharmaceutical composition comprising a pharmaceutically acceptable carrier or excipient.

131. The method of claim 126, wherein said RXR agonist, said PPARγ agonist and said compound are administered to said host in a pharmaceutical composition comprising a pharmaceutically acceptable carrier or excipient.

132. The method of claim 128, 129, 130 or 131, wherein said pharmaceutical composition consists of a single dosage unit.

133. A method of preventing hyperinsulinemia in a host with propensity thereof, comprising the step of administering to said host a pharmaceutically effective amount of an RXR agonist.

134. The method of claim 133, wherein said RXR agonist is an RXR specific agonist.

135. The method of claim 134, wherein said RXR specific agonist is 2-[1-(3,5,5,8,8-pentamethyl-5,6,7,8-tetrahydro-2-naphthyl)-cyclopropyl]-pyridine-5-carboxylic acid or a pharmaceutically acceptable salt thereof.

136. The method of claim 134, wherein said RXR specific agonist is 4-[(3,5,5,8,8-pentamethyl-5,6,7,8-tetrahydro-2-naphthyl)-2-carbonyl]-benzoic acid or a pharmaceutically acceptable salt thereof.

137. The method of claim 133, further comprising the step of administering to said host a pharmaceutically effective amount of a PPARγ agonist.

138. The method of claim 137, wherein said PPARγ agonist is a thiazolidinedione compound.

139. The method of claim 138, wherein said thiazolidinedione compound is selected from the group consisting of 5-[[4-[2-(methyl-2-pyridinylamino)ethoxy]phenyl]methyl]-2,4-thiazolidinedione, troglitazone, pioglitazone, ciglitazone, WAY-120,744, englitazone, AD 5075, darglitazone, and their pharmaceutically acceptable salts.

140. The method of claim 133, further comprising the step of administering to said host a pharmaceutically effective amount of a compound selected from the group consisting of insulin, an insulin derivative, an insulin secretagogue, an insulin sensitizer, and an insulin mimetic.

141. The method of claim 137, further comprising the step of administering to said host a pharmaceutically effective amount of a compound selected from the group consisting of insulin, an insulin derivative, an insulin secretagogue, an insulin sensitizer, and an insulin mimetic.

142. The method of claim 133, wherein said RXR agonist is orally, topically, intravenously, transdermally, rectally, or parentally administered to said host.

143. The method of claim 133, wherein said RXR agonist is administered to said host in a pharmaceutical composition comprising a pharmaceutically acceptable carrier or excipient.

144. The method of claim 137, wherein said RXR agonist and said PPARγ agonist are administered to said host in a pharmaceutical composition comprising a pharmaceutically acceptable carrier or excipient.

145. The method of claim 140, wherein said RXR agonist and said compound are administered to said host in a pharmaceutical composition comprising a pharmaceutically acceptable carrier or excipient.

146. The method of claim 141, wherein said RXR agonist, said PPARγ agonist and said compound are administered to said host in a pharmaceutical composition comprising a pharmaceutically acceptable carrier or excipient.

147. The method of claim 143, 144, 145 or 146, wherein said pharmaceutical composition consists of a single dosage unit.

148. A method of enhancing the antihyperglycemic activity of a thiazolidinedione compound in treating a host suffering from hyperglycemia, comprising the step of administering to said host a pharmaceutically effective amount of an RXR agonist and a pharmaceutically effective amount of said thiazolidinedione compound.

149. The method of claim 148, wherein said RXR agonist is an RXR specific agonist.

150. The method of claim 149, wherein said RXR specific agonist is 2-[1-(3,5,5,8,8-pentamethyl-5,6,7,8-tetrahydro-2-naphthyl)-cyclopropyl]-pyridine-5-carboxylic acid or a pharmaceutically acceptable salt thereof.

151. The method of claim 149, wherein said RXR specific agonist is 4-[(3,5,5,8,8-pentamethyl-5,6,7,8-tetrahydro-2-naphthyl)-2-carbonyl]-benzoic acid or a pharmaceutically acceptable salt thereof.

152. The method of claim 148, further comprising the step of administering to said host a pharmaceutically effective amount of a PPARγ agonist.

153. The method of claim 152, wherein said PPARγ agonist is said thiazolidinedione compound.

154. The method of claim 153, wherein said thiazolidinedione compound is selected from the group consisting of 5-[[4-[2-(methyl-2-pyridinylamino)ethoxy]phenyl]methyl]-2,4-thiazolidinedione, troglitazone, pioglitazone, ciglitazone, WAY-120,744, englitazone, AD 5075, darglitazone, and their pharmaceutically acceptable salts.

155. The method of claim 148, further comprising the step of administering to said host a pharmaceutically effective amount of a compound selected from the group consisting of insulin, an insulin derivative, an insulin secretagogue, an insulin sensitizer, and an insulin mimetic.

156. The method of claim 152, further comprising the step of administering to said host a pharmaceutically effective amount of a compound selected from the group consisting of insulin, an insulin derivative, an insulin secretagogue, an insulin sensitizer, and an insulin mimetic.

157. The method of claim 148, wherein said RXR agonist is orally, topically, intravenously, transdermally, rectally, or parentally administered to said host.

158. The method of claim 148, wherein said RXR agonist is administered to said host in a pharmaceutical composition comprising a pharmaceutically acceptable carrier or excipient.

159. The method of claim 152, wherein said RXR agonist and said PPARγ agonist are administered to said host in a pharmaceutical composition comprising a pharmaceutically acceptable carrier or excipient.

160. The method of claim 155, wherein said RXR agonist and said compound are administered to said host in a pharmaceutical composition comprising a pharmaceutically acceptable carrier or excipient.

161. The method of claim 156, wherein said RXR agonist, said PPARγ agonist and said compound are administered to said host in a pharmaceutical composition comprising a pharmaceutically acceptable carrier or excipient.

162. The method of claim 158, 159, 160 or 161, wherein said pharmaceutical composition consists of a single dosage unit.

* * * * *